US012257056B2

(12) United States Patent
Parker et al.

(10) Patent No.: US 12,257,056 B2
(45) Date of Patent: *Mar. 25, 2025

(54) METHOD AND APPARATUS FOR MEASUREMENT OF NEURAL RESPONSE

(71) Applicant: Saluda Medical Pty Ltd, Artarmon (AU)

(72) Inventors: John Louis Parker, Macquarie Park (AU); Peter Scott Vallack Single, Macquarie Park (AU); Dean Michael Karantonis, Macquarie Park (AU)

(73) Assignee: Saluda Medical Pty Ltd, Macquarie Park (AU)

( * ) Notice: Subject to any disclaimer, the term of this patent is extended or adjusted under 35 U.S.C. 154(b) by 0 days.

This patent is subject to a terminal disclaimer.

(21) Appl. No.: 18/738,925

(22) Filed: Jun. 10, 2024

(65) Prior Publication Data
US 2024/0324928 A1    Oct. 3, 2024

Related U.S. Application Data

(63) Continuation of application No. 17/729,158, filed on Apr. 26, 2022, which is a continuation of application (Continued)

(30) Foreign Application Priority Data

May 13, 2011   (AU) .................. 2011901817

(51) Int. Cl.
*A61B 5/24*      (2021.01)
*A61B 5/00*      (2006.01)
(Continued)

(52) U.S. Cl.
CPC .............. *A61B 5/24* (2021.01); *A61B 5/4848* (2013.01); *A61B 5/6846* (2013.01);
(Continued)

(58) Field of Classification Search
CPC ....... A61B 5/24; A61B 5/4848; A61B 5/6846; A61B 5/7285; A61B 5/7203;
(Continued)

(56) References Cited

U.S. PATENT DOCUMENTS 5,702,429 A    12/1997    King
5,758,651 A    6/1998     Nygard
(Continued)

FOREIGN PATENT DOCUMENTS

WO   WO2004021885        3/2004
WO   WO2009046764 A1    4/2009
(Continued)

OTHER PUBLICATIONS

Al-ani et al., "Automatic removal of high-amplitude stimulus artefact from neuronal signal recorded in the subthalamic nucleus", Journal of Neuroscience Methods, vol. 198, Issue 1, 2011, pp. 135-146.
(Continued)

*Primary Examiner* — Patrick Fernandes
(74) *Attorney, Agent, or Firm* — Barnes & Thornburg LLP

(57) ABSTRACT

A method for measuring a neural response to a stimulus. Measurement circuitry is settled prior to a stimulus, by connecting a sense electrode to the measurement circuitry to allow the measurement circuitry to settle towards a bioelectrically defined steady state. Charge is recovered on stimulus electrodes by short circuiting the stimulus electrodes to each other. An electrical stimulus is then applied from the stimulus electrodes to neural tissue, while keeping the sense electrode disconnected from the measurement circuitry. After the stimulus, a delay is imposed during which the stimulus electrodes are open circuited and the sense electrode is disconnected from the measurement circuitry
(Continued)

and from the stimulus electrodes. After the delay, a neural response signal present at the sense electrode is measured by connecting the sense electrode to the measurement circuitry.

26 Claims, 23 Drawing Sheets

Related U.S. Application Data

No. 16/391,181, filed on Apr. 22, 2019, now Pat. No. 11,324,427, which is a continuation of application No. 15/184,787, filed on Jun. 16, 2016, now Pat. No. 10,278,600, which is a continuation of application No. 14/117,144, filed as application No. PCT/AU2012/000511 on May 11, 2012, now Pat. No. 9,386,934.

(51) Int. Cl.
  A61M 5/172 (2006.01)
  A61N 1/36 (2006.01)

(52) U.S. Cl.
  CPC ......... *A61B 5/7285* (2013.01); *A61M 5/1723* (2013.01); *A61N 1/36071* (2013.01); *A61N 1/36125* (2013.01); *A61N 1/36135* (2013.01); *A61N 1/36146* (2013.01); *A61B 5/7203* (2013.01); *A61M 2230/08* (2013.01)

(58) Field of Classification Search
  CPC .. A61B 5/4836; A61B 5/4041; A61M 5/1723; A61M 2230/08; A61N 1/36071; A61N 1/36125; A61N 1/36135; A61N 1/36146; A61N 1/0551; A61N 1/36185; A61N 1/36139
  See application file for complete search history.

(56) References Cited

U.S. PATENT DOCUMENTS

| 5,792,212 | A  | 8/1998  | Weijand       |
| 5,814,092 | A  | 9/1998  | King          |
| 5,913,882 | A  | 6/1999  | King          |
| 6,473,649 | B1 | 10/2002 | Gryzwa et al. |
| 7,171,261 | B1 | 1/2007  | Litvak et al. |
| 7,283,877 | B1 | 10/2007 | Litvak et al. |
| 7,447,549 | B2 | 11/2008 | Litvak et al. |
| 11,259,732 | B2 | 3/2022 | Parramon et al. |
| 2005/0101878 | A1 | 5/2005 | Daly et al. |
| 2007/0225767 | A1 | 9/2007 | Daly et al. |
| 2007/0244410 | A1 | 10/2007 | Fridman et al. |
| 2010/0100153 | A1 | 4/2010 | Carlson et al. |

FOREIGN PATENT DOCUMENTS

| WO | WO2010032132 A4 | 6/2010  |
| WO | WO2011159545 A2 | 12/2011 |

OTHER PUBLICATIONS

Blum, A. R., "An Electronic System for Extracellular Neural Stimulation and Recording", Dissertation, Georgia Institute of Technology, Aug. 2007, Retrieved from http://smartech.gatech.edu/handle/1853/16192 on Jan. 30, 2012.

Budagavi et al., "Modelling of compound nerve action potentials health and disease", Engineering in Medicine and Biology Society, 1992 14th Annual International Conference of the IEEE. vol. 6. IEEE, 1992. pp. 2600-2601.

Dillier, N, et al., "Measurement of the electrically evoked compound action potential via a neural response telemetry system", Ann. Otol. Rhinol. Laryngol., vol. 111, No. 5, May 2002, pp. 407-414.

Gnadt et al., "Spectral Cancellation of Microstimulation Artifact for Simultaneous Neural Recording In Situ", IEEE Transactions on Biomedical Engineering, Oct. 2003, Date of Publication: Sep. 23, 2003, vol. 50, No. 10, pp. 1129-1135, DOI: 10.1109/TBME.2003.816077.

Kim et al., "A Wavelet-Based Method for Action Potential Detection From Extracellular Neural Signal Recording With Low Signal-to-Noise Ratio", IEEE Transactions On Biomedical Engineering, Aug. 2003, vol. 50. No. 8, pp. 999-1011.

McGill et al., "On the Nature and Elimination of Stimulus Artifact in Nerve Signals Evoked and Recorded Using Surface Electrodes", IEEE Transactions On Biomedical Engineering, vol. BME-29, No. 2, Feb. 1982.

Mens, Lucas, "Advances in Cochlear Implant Telemetry: Evoked Neural Responses, Electrical Field Imaging, and Technical Integrity", Trends in Amplification, vol. 11, No. 3, Sep. 2007 143-159.

Shepherd et al., "Electrical stimulation of the auditory nerve: II. Effect of stimulus waveshape on single fibre response properties", Hearing Research, 1999, 130, 171-188.

Yuan, S. et al., "Recording monophasic action potentials using a platinum-electrode ablation catheter", Europace. Oct. 2000; 2(4):312-319.

METHOD AND APPARATUS FOR MEASUREMENT OF NEURAL RESPONSE

CROSS-REFERENCE TO RELATED APPLICATIONS

This application is a continuation of U.S. application Ser. No. 17/729,158, filed Apr. 26, 2022, which is a continuation of U.S. application Ser. No. 16/391,181, filed Apr. 22, 2019 and issued on May 10, 2022 as U.S. Pat. No. 11,324,427, which is a continuation of U.S. application Ser. No. 15/184,787, filed Jun. 16, 2016 and issued on May 7, 2019 as U.S. Pat. No. 10,278,600, which is a continuation of U.S. application Ser. No. 14/117,144, filed Nov. 12, 2013 and issued on Jul. 12, 2016 as U.S. Pat. No. 9,386,934, which application is a national stage of Application No. PCT/AU2012/000511, filed May 11, 2012, which application claims the benefit of Australian Provisional Patent Application No. 2011901817, filed May 13, 2011, the disclosures of which are incorporated herein by reference in their entirety.

TECHNICAL FIELD

The present invention relates to measurement of a neural response to a stimulus, and in particular relates to measurement of a compound action potential by using one or more electrodes implanted proximal to the neural pathway.

BACKGROUND OF THE INVENTION

Neuromodulation is used to treat a variety of disorders including chronic pain, Parkinson's disease, and migraine. A neuromodulation system applies an electrical pulse to tissue in order to generate a therapeutic effect. When used to relieve chronic pain, the electrical pulse is applied to the dorsal column (DC) of the spinal cord or dorsal root ganglion (DRG). Such a system typically comprises an implanted electrical pulse generator, and a power source such as a battery that may be rechargeable by transcutaneous inductive transfer. An electrode array is connected to the pulse generator, and is positioned in the dorsal epidural space above the dorsal column. An electrical pulse applied to the dorsal column by an electrode causes the depolarisation of neurons, and generation of propagating action potentials. The fibres being stimulated in this way inhibit the transmission of pain from that segment in the spinal cord to the brain.

While the clinical effect of spinal cord stimulation (SCS) is well established, the precise mechanisms involved are poorly understood. The DC is the target of the electrical stimulation, as it contains the afferent Aβ fibres of interest. Aβ fibres mediate sensations of touch, vibration and pressure from the skin. The prevailing view is that SCS stimulates only a small number of Aβ fibres in the DC. The pain relief mechanisms of SCS are thought to include evoked antidromic activity of Aβ fibres having an inhibitory effect, and evoked orthodromic activity of Aβ fibres playing a role in pain suppression. It is also thought that SCS recruits Aβ nerve fibres primarily in the DC, with antidromic propagation of the evoked response from the DC into the dorsal horn thought to synapse to wide dynamic range neurons in an inhibitory manner.

Neuromodulation may also be used to stimulate efferent fibres, for example to induce motor functions. In general, the electrical stimulus generated in a neuromodulation system triggers a neural action potential which then has either an inhibitory or excitatory effect. Inhibitory effects can be used to modulate an undesired process such as the transmission of pain, or to cause a desired effect such as the contraction of a muscle.

The action potentials generated among a large number of fibres sum to form a compound action potential (CAP). The CAP is the sum of responses from a large number of single fibre action potentials. The CAP recorded is the result of a large number of different fibres depolarising.

The propagation velocity is determined largely by the fibre diameter and for large myelinated fibres as found in the dorsal root entry zone (DREZ) and nearby dorsal column the velocity can be over 60 ms$^{-1}$. The CAP generated from the firing of a group of similar fibres is measured as a positive peak potential P1, then a negative peak N1, followed by a second positive peak P2. This is caused by the region of activation passing the recording electrode as the action potentials propagate along the individual fibres.

To better understand the effects of neuromodulation and/or other neural stimuli, it is desirable to record a CAP resulting from the stimulus. However, this can be a difficult task as an observed CAP signal will typically have a maximum amplitude in the range of microvolts, whereas a stimulus applied to evoke the CAP is typically several volts. Electrode artefact usually results from the stimulus, and manifests as a decaying output of several millivolts throughout the time that the CAP occurs, presenting a significant obstacle to isolating the CAP of interest. Some neuromodulators use monophasic pulses and have capacitors to ensure there is no DC flow to the tissue. In such a design, current flows through the electrodes at all times, either stimulation current or equilibration current, hindering spinal cord potential (SCP) measurement attempts. Moreover, high-pass filter poles in measurement circuitry generate increased electrical artefact with mono-phasic pulses. The capacitor recovers charge at the highest rate immediately after the stimulus, undesirably causing greatest artefact at the same time that the evoked response occurs.

To resolve a 10 uV SCP with 1 uV resolution in the presence of an input 5V stimulus, for example, requires an amplifier with a dynamic range of 134 dB, which is impractical in implant systems. As the neural response can be contemporaneous with the stimulus and/or the stimulus artefact, CAP measurements present a difficult challenge of amplifier design. In practice, many non-ideal aspects of a circuit lead to artefact, and as these mostly have a decaying exponential appearance that can be of positive or negative polarity, their identification and elimination can be laborious.

A number of approaches have been proposed for recording a CAP. King (U.S. Pat. No. 5,913,882) measures the spinal cord potential (SCP) using electrodes which are physically spaced apart from the stimulus site. To avoid amplifier saturation during the stimulus artefact period, recording starts at least 1-2.5 ms after the stimulus. At typical neural conduction velocities, this requires that the measurement electrodes be spaced around 10 cm or more away from the stimulus site, which is undesirable as the measurement then necessarily occurs in a different spinal segment and may be of reduced amplitude.

Nygard (U.S. Pat. No. 5,758,651) measures the evoked CAP upon an auditory nerve in the cochlea, and aims to deal with artefacts by a sequence which comprises: (1) equilibrating electrodes by short circuiting stimulus electrodes and a sense electrode to each other; (2) applying a stimulus via the stimulus electrodes, with the sense electrode being open circuited from both the stimulus electrodes and from the measurement circuitry; (3) a delay, in which the stimulus electrodes are switched to open circuit and the sense electrode remains open circuited; and (4) measuring, by switching the sense electrode into the measurement circuitry. Nygard also teaches a method of nulling the amplifier following the stimulus. This sets a bias point for the amplifier during the period following stimulus, when the electrode is not in equilibrium. As the bias point is reset each cycle, it is susceptible to noise. The Nygard measurement amplifier is a differentiator during the nulling phase which makes it susceptible to pickup from noise and input transients when a non-ideal amplifier with finite gain and bandwidth is used for implementation.

Daly (US Patent Application No. 2007/0225767) utilizes a biphasic stimulus plus a third phase "compensatory" stimulus which is refined via feedback to counter stimulus artefact. As for Nygard, Daly's focus is the cochlea. Daly's measurement sequence comprises (1) a quiescent phase where stimulus and sense electrodes are switched to $V_{dd}$; (2) applying the stimulus and then the compensatory phase, while the sense electrodes are open circuited from both the stimulus electrodes and from the measurement circuitry; (3) a load settling phase of about 1 μs in which the stimulus electrodes and sense electrodes are shorted to $V_{dd}$; and (4) measurement, with stimulus electrodes open circuited from $V_{dd}$ and from the current source, and with sense electrodes switched to the measurement circuitry. However a 1 μs load settling period is too short for equilibration of electrodes which typically have a time constant of around 100 μs. Further, connecting the sense electrodes to $V_{dd}$ pushes charge onto the sense electrodes, exacerbating the very problem the circuit is designed to address.

Evoked responses are less difficult to detect when they appear later in time than the artifact, or when the signal-to-noise ratio is sufficiently high. The artifact is often restricted to a time of 1-2 ms after the stimulus and so, provided the neural response is detected after this time window, data can be obtained. This is the case in surgical monitoring where there are large distances between the stimulating and recording electrodes so that the propagation time from the stimulus site to the recording electrodes exceeds 2 ms. Because of the unique anatomy and tighter coupling in the cochlea, cochlear implants use small stimulation currents relative to the tens of mA sometimes required for SCS, and thus measured signals in cochlear systems present a relatively lower artifact. However to characterize the responses from the dorsal columns, high stimulation currents and close proximity between electrodes are required, and therefore the measurement process must overcome artifact directly, in contrast to existing "surgical monitoring" techniques.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SUMMARY OF THE INVENTION

According to a first aspect the present invention provides a method for measuring a neural response to a stimulus, the method comprising:

settling measurement circuitry prior to a stimulus, by connecting a sense electrode to the measurement circuitry to allow the measurement circuitry to settle towards a bio-electrically defined steady state;

recovering charge on stimulus electrodes by short circuiting the stimulus electrodes to each other;

applying an electrical stimulus from the stimulus electrodes to neural tissue, while keeping the sense electrode disconnected from the measurement circuitry;

imposing a delay during which the stimulus electrodes are open circuited and the sense electrode is disconnected from the measurement circuitry and from the stimulus electrodes; and after the delay, measuring a neural response signal present at the sense electrode by connecting the sense electrode to the measurement circuitry.

According to a second aspect the present invention provides an implantable device for measuring a neural response to a stimulus, the device comprising:

a plurality of electrodes including one or more nominal stimulus electrodes and one or more nominal sense electrodes;

a stimulus source for providing a stimulus to be delivered from the one or more stimulus electrodes to neural tissue;

measurement circuitry for amplifying a neural signal sensed at the one or more sense electrodes; and a control unit configured to control application of a stimulus to the neural tissue and measurement of an evoked neural response, the control unit configured to settle the measurement circuitry prior to a stimulus by connecting the or each sense electrode to the measurement circuitry to allow the measurement circuitry to settle towards a bio-electrically defined steady state, the control unit further configured to recover charge on the stimulus electrodes by short circuiting the stimulus electrodes to each other, the control unit further configured to cause the stimulus source to apply an electrical stimulus from the stimulus electrodes to neural tissue while keeping the or each sense electrode disconnected from the measurement circuitry, the control unit further configured to impose a delay during which the stimulus electrodes are open circuited and the sense electrode is disconnected from the measurement circuitry and from the stimulus electrodes, and the control unit further configured to measure a neural response signal present at the sense electrode by connecting the or each sense electrode to the measurement circuitry after the delay.

It is to be understood herein that open circuiting of an electrode involves ensuring that the electrode is disconnected from other electrodes, the stimulus source, the measurement circuitry and from voltage rails. Ensuring that the sense electrode is disconnected from the stimulus electrodes during the delay period avoids charge transfer onto the sense electrode(s) and associated artefact. The present invention recognizes that connecting the sense electrodes to the stimulus electrodes during a post-stimulus delay period can undesirably give rise to such charge transfer and associated artefact, particularly if the delay is short relative to the time constant of the stimulus electrodes, the latter typically being around 100 μs. The sense electrode is preferably open circuited during the post-stimulus delay so as to be disconnected from all other electrodes of the array, to prevent such charge transfer to the sense electrode from other non-stimulus electrodes. With particular regard to the case of spinal cord response measurement, the present invention recognizes that in the spinal cord, the stimulation electrodes may never reach equilibrium at the stimulation rates used for chronic pain, so that connecting them to the stimulating electrodes at any time would increase artefact. This lack of equilibrium is due to the nature of the Helmholtz layer which causes fractional pole variation in the electrode impedance with frequency, with time constants as long as tens of milliseconds.

The present invention recognizes that it is beneficial to provide for pre-stimulus settling of the measurement circuitry towards a bio-electrically defined steady state. This ensures that charge recovery occurs in the settling stage prior to the stimulus and not during or immediately after the stimulus and thus does not give rise to artefact during or immediately after the stimulus. Thus, the present invention captures the bio-electrically defined steady state as reference point voltage at the end of the measurement cycle, when the system is in its most stable state. The system then amplifies the difference between the captured voltage and the reference point voltage. Where repeated measurement cycles are undertaken, the present invention further permits the measurement amplifier to accumulate a bias point over multiple cycles rather than re-setting the bias point each cycle. The settle period is preferably sufficiently long to permit the electrodes and circuitry to reach an equilibrium, and for example the settle period may be around 1 ms or greater, as permitted by a stimulus rate. For example if therapeutic stimuli are applied to a dorsal column at about 100 Hz and do not give rise to a slow neural response, then after the approximately 2 ms duration of an evoked fast response up to about 8 ms would be available for the settling period. However, this is generally longer than required and the settling period may be substantially less than 8 ms.

The delay may be in the range of substantially zero to 1 ms, and for example may be about 0.3 ms. Such embodiments permit onset of the neural response to be observed, this typically occurring about 0.3 ms after the stimulus for an electrode 3 cm away from the stimulus site. In embodiments in which an amplifier of the measurement circuitry has a very high dynamic range, and/or if using a measurement electrode closer to the stimulus electrode, the delay may be set to a smaller value for example in the range of 50-200 μs. The delay is preferably set to a value which ensures the measurement amplifier is not saturated and therefore performs linearly at all times when connected without experiencing clipping, and for example a feedback loop may be implemented to determine a suitable delay which avoids amplifier saturation for a given stimulus.

In preferred embodiments of the invention, the signal from the or each sense electrode is passed to a sample-and-hold circuit at the input of a measurement amplifier. In such embodiments measurements of a single evoked response may be obtained from a plurality of sense electrodes, even if the measurement circuitry of each electrode is connected to the control unit only by a two wire bus or the like, as is commonly required in implanted electrode arrays.

Additionally or alternatively, a buffer or follower amplifier is preferably provided in some embodiments, between the sense electrode and the measurement amplifier. The buffer is preferably connected to the sense electrode without interposed switches, so that the high reverse impedance of the buffer effectively prevents switching transients from being conveyed to the sense electrode, thereby avoiding artefact which may arise upon the sense electrode if subjected to such transients. The buffer amplifier is also preferably configured to give current gain to drive a storage capacitor of a sample and hold circuit. A series capacitor may be interposed between the sense electrode and the buffer to avoid DC transfer with the tissue in the event where the amplifier malfunctions. This capacitor also allows the bias voltage of the amplifier to equilibrate as the electrode voltage can drift over time periods of several tens of seconds.

In preferred embodiments of the invention, the stimulus and sense electrodes are selected from an implanted electrode array. The electrode array may for example comprise a linear array of electrodes arranged in a single column along the array. Alternatively the electrode array may comprise a two dimensional array having two or more columns of electrodes arranged along the array. Preferably, each electrode of the electrode array is provided with an associated measurement amplifier, to avoid the need to switch the sense electrode(s) to a shared measurement amplifier, as such switching can add to measurement artefact. Providing a dedicated measurement amplifier for each sense electrode is further advantageous in permitting recordings to be obtained from multiple sense electrodes simultaneously.

The measurement may be a single-ended measurement obtained by passing a signal from a single sense electrode to a single-ended amplifier. Alternatively, the measurement may be a differential measurement obtained by passing signals from two sense electrodes to a differential amplifier.

While recovering charge by short circuiting the stimulus electrodes together, it may in some embodiments be advantageous to disconnect the sense electrode from the measurement circuitry, for example by setting a sample-and-hold circuit to "hold".

Embodiments of the invention may prove beneficial in obtaining a CAP measurement which has lower dynamic range and simpler morphology as compared to systems more susceptible to artefact. Such embodiments of the present invention may thus reduce the dynamic range requirements of implanted amplifiers, and may avoid or reduce the complexity of signal processing systems for feature extraction, simplifying and miniaturizing an implanted integrated circuit. Such embodiments may thus be particularly applicable for an automated implanted evoked response feedback system for stimulus control. Thus, in a further aspect, the present invention provides a method for feedback control of a neural stimulus, the method comprising an implanted control unit obtaining a CAP measurement in accordance with the method of the first aspect, and the implanted control unit using the obtained CAP measurement to control the delivery of subsequent neural stimuli by the implant.

In some embodiments of the invention, an averaged CAP measurement may be obtained by (i) delivering a first biphasic stimulus which starts with a pulse of a first polarity and then delivers a pulse of a second polarity opposite to the first polarity, and obtaining a first measurement of a CAP evoked by the first stimulus; (ii) delivering a second biphasic stimulus which starts with a pulse of the second polarity and then delivers a pulse of the first polarity, and obtaining a second measurement of a CAP evoked by the second stimulus; and (iii) taking an average of the first measurement and the second measurement to obtain an averaged measurement. Such embodiments exploit the observation that artefact polarity usually reflects the stimulus polarity, whereas the CAP polarity is independent of the stimulus polarity and is instead determined by the anatomy and physiology of the spinal cord membrane, so that averaging the first and second measurements will tend to selectively cancel out artefact. Further noting that for some electrode polarity configurations, such as monopolar, an "anodic first" biphasic stimulus usually has a lower stimulus threshold for neural recruitment than a "cathodic first" biphasic stimulus, the averaged measurement may have a morphology of either (i) a typical CAP of half amplitude if only the anodic-first stimulus exceeds the stimulus threshold; (ii) the average of two CAPs of different amplitude if both stimuli exceed the stimulus threshold but the cathodic first stimulus does not cause saturation recruitment; or (iii) a typical CAP if both stimuli exceed saturation recruitment. Some embodiments may therefore obtain a curve of the averaged measurement vs. stimulus amplitude in order to obtain information regarding the recruitment effected by each stimulus, and such information may be used for feedback control by the implant.

In some embodiments, the method of the present invention may be applied contemporaneously with administration of a drug, in order to gauge efficacy of drug delivery. For example, the implant may comprise or be operatively connected to a drug reservoir and drug delivery pump, with the pump being controlled by feedback based on CAP measurements.

According to another aspect the present invention provides a computer program product comprising computer program code means to make an implanted processor execute a procedure for measuring a neural response to a stimulus, the computer program product comprising computer program code means for carrying out the method of the first aspect.

The present invention recognises that when considering spinal cord stimulation, obtaining information about the activity within the spinal segment where stimulation is occurring is highly desirable. Observing the activity and extent of propagation both above (rostrally of) and below (caudally of) the level of stimulation is also highly desirable. The present invention recognises that in order to record the evoked activity within the same spinal segment as the stimulus requires an evoked potential recording system which is capable of recording an SCP within approximately 3 cm of its source, i.e. within approximately 0.3 ms of the stimulus, and further recognises that in order to record the evoked activity using the same electrode array as applied the stimulus requires an evoked potential recording system which is capable of recording an SCP within approximately 7 cm of its source, i.e. within approximately 0.7 ms of the stimulus.

In preferred embodiments the stimulus comprises a biphasic pulse, and the stimulus electrodes have no capacitors. In contrast to a monophasic pulse and capacitor arrangement, such embodiments permit the stimulus electrode current to be interrupted, or forced to zero, at those times where it would interfere with measurement. Omitting capacitors is also desirable in order to minimise the size of the implanted device.

BRIEF DESCRIPTION OF THE DRAWINGS

An example of the invention will now be described with reference to the accompanying drawings, in which.

DESCRIPTION OF THE PREFERRED EMBODIMENTS

Figure 1:
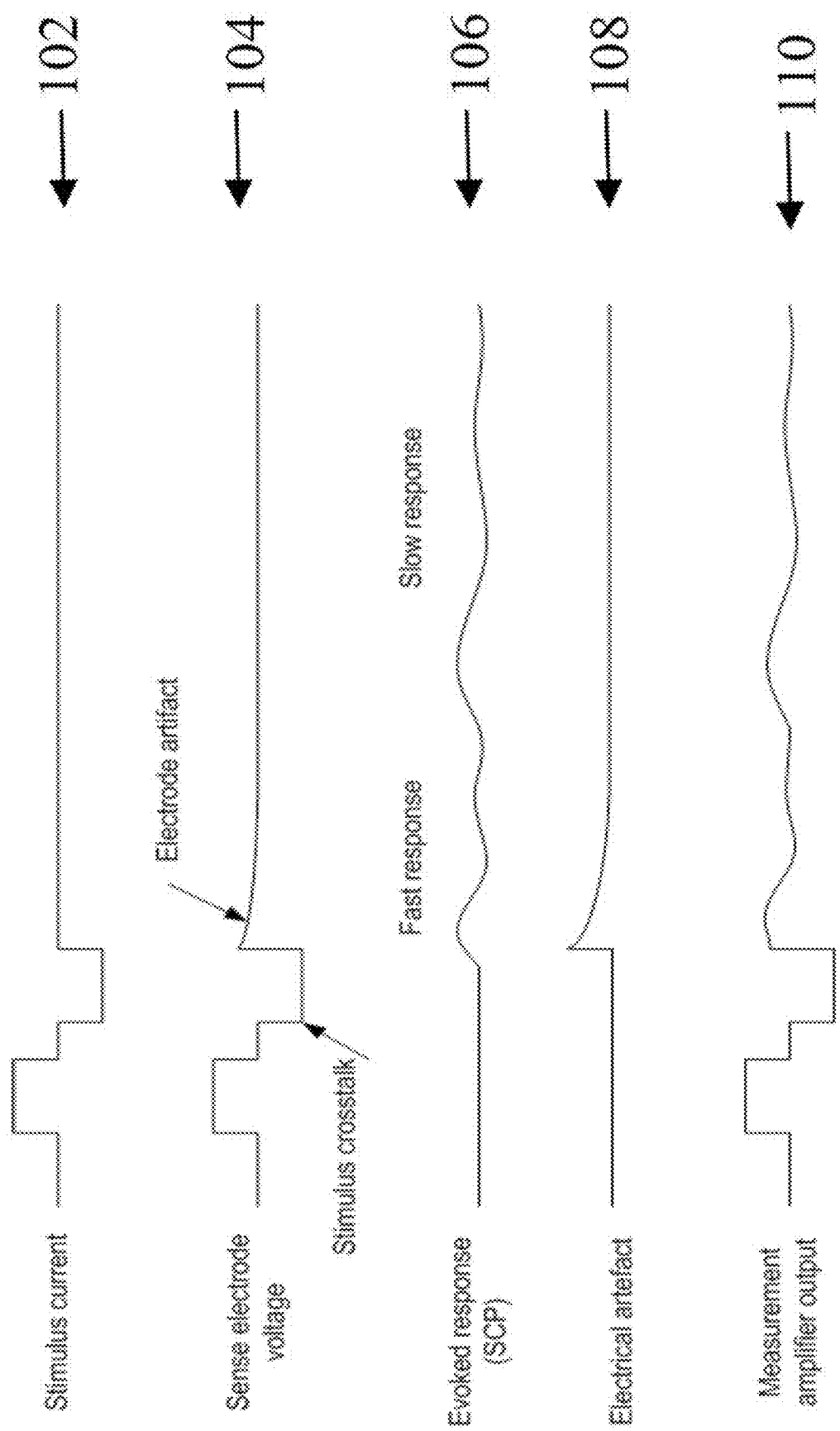
FIG. 1 illustrates currents and voltages which can contribute to SCP measurements.

FIG. 1 shows the currents and voltages that contribute to SCP measurements. These signals include the stimulus current 102 applied by two stimulus electrodes, which is a charge-balanced biphasic pulse to provide low artefact. Alternative embodiments may instead use three electrodes to apply a tripolar charge balanced stimulus. In the case of spinal cord stimulation, the stimulus currents 102 used to provide paraesthesia and pain relief typically consist of pulses in the range of 3-30 mA amplitude, with pulse width typically in the range of 100-400 μs, or alternatively may be paraesthesia-free such as neuro or escalator style stimuli. The stimuli can comprise monophasic or biphasic pulses.

The stimulus 102 induces a voltage on adjacent electrodes, referred to as stimulus crosstalk 104. Where the stimuli 102 are SCP stimuli they typically induce a voltage 104 in the range of about 1-5 V on a SCP sense electrode.

The stimulus 102 also induces electrode artefact, which is a residual voltage on an electrode resulting from uneven charge distribution on its surface. The electrode artefact is indicated in the voltage waveform 104 after cessation of stimulus crosstalk. The stimulus 102 disturbs the galvanic interface between the sense electrode and the tissue, so that after stimulus crosstalk in voltage 104 concludes, a voltage known as the electrode artefact continues on the electrode, as indicated in waveform 104 in FIG. 1. Electrode artefact is very difficult to measure, and depends on factors such as the stimulation pulse, the geometry of the electrodes and the bio-electrical nature of the tissue surrounding the electrodes. Electrode artefact can have a typical value of 500 µV at a time 50 µs after stimulation ceases. Electrode artefact is difficult to measure because it is indistinguishable from electrical artefact, the latter being caused by the amplifier's exposure to the high stimulation voltages. Further, the causes of electrical artefact can be subtle, and therefore hard to identify and eliminate.

An appropriate stimulus 102 will also induce nerves to fire, and thereby produces an evoked neural response 106. In the spinal cord, the neural response 106 has two major components: a fast response lasting ~2 ms and a slow response lasting ~15 ms. The slow response only appears at stimulation amplitudes which are larger than the minimum stimulus required to elicit a fast response. The amplitude of the evoked response seen by epidural electrodes is typically no more than hundreds of microvolts, but in some clinical situations can be only tens of microvolts.

In practical implementation a measurement amplifier used to measure the evoked response does not have infinite bandwidth, and will normally have infinite impulse response filter poles, and so the stimulus crosstalk 104 will produce an output 108 during the evoked response 106, this output being referred to as electrical artefact.

Electrical artefact can be in the hundreds of millivolts as compared to a SCP of interest in the tens of microvolts. Electrical artefact can however be reduced by suitable choice of a high-pass filter pole frequency.

The measurement amplifier output 110 will therefore contain the sum of these various contributions 102-108. Separating the evoked response of interest (106) from the artefacts 104 and 108 is a major technical challenge. For example, to resolve a 10 µV SCP with 1 µV resolution, and have at the input a 5V stimulus, requires an amplifier with a dynamic range of 134 dB. As the response can overlap the stimulus this represents a difficult challenge of amplifier design.

FIG. 2A, FIG. 2B, FIG. 2C, FIG. 2D, and FIG. 2E are schematic diagrams of the five phases of operation of a sample and hold (S/H) measurement amplifier in accordance with one embodiment of the present invention. The stimulus and measurement circuitry 200 comprises a buffer amplifier 206 that is always connected to the sense electrode 202 such that there is no switch between the sense electrode 202 and the buffer amplifier 206. The output of the buffer amplifier 206 drives a sample and hold circuit 208, followed by a high gain amplifier 210 with unity gain at DC. The front-end amplifier 206 has sufficiently wide bandwidth that it can follow the voltage induced on the sense electrodes 202 by the stimulus pulse, and settle before the SCP begins. A current source 212 can be selectively connected to stimulus electrodes 204 to deliver a stimulus. The stimulus electrodes 204 and sense electrode 202 are in the same electrode array of a single implanted device.

The stimulus and measurement circuitry 200 operates to obtain a SC measurement using five phases. The first phase shown in FIG. 2A open circuits the stimulus electrodes 204 and connects the sense electrode 202 to the measurement amplifier 210 by setting the sample and hold circuit to "sample". The first phase shown in FIG. 2A allows the amplifier chain 206, 210 to settle, with no disturbance from the stimulating electrodes 204.

Figure 2A:
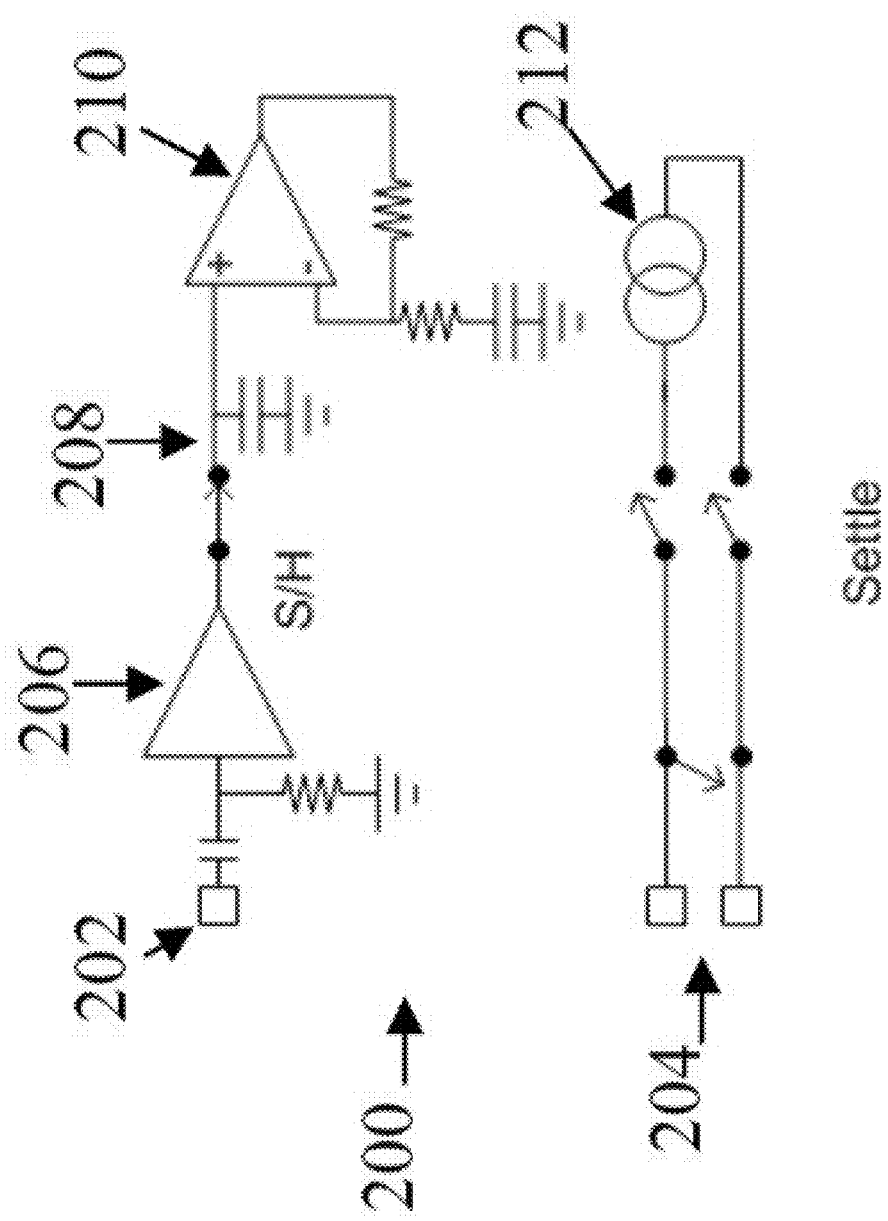
FIG. 2A illustrates the circuitry of one embodiment of the present invention during the settle phase of a measurement cycle.
Figure 2B:
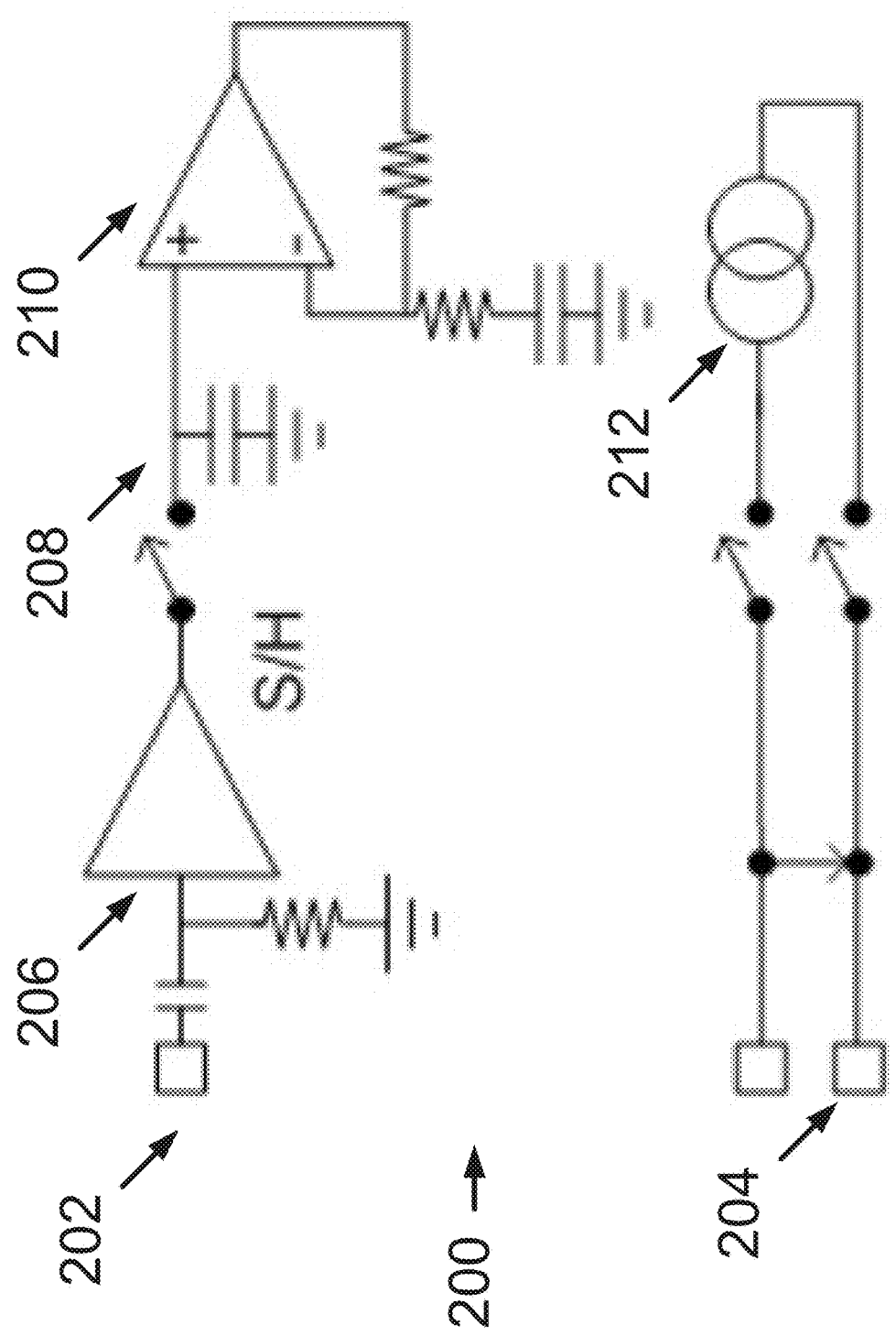
FIG. 2B illustrates the circuitry of one embodiment of the present invention during the charge recovery phase of a measurement cycle.

In the second phase shown in FIG. 2B, the stimulus electrodes 204 are short circuited to each other. This allows the stimulating electrodes 204 to recover charge, so as to avoid DC injection to the tissue as is required for electrical implants. During this phase, the sample-and-hold 208 is set to "hold" so that charge transfer on the stimulus electrodes 204 does not disrupt the measurement amplifier 210.

Figure 2C:
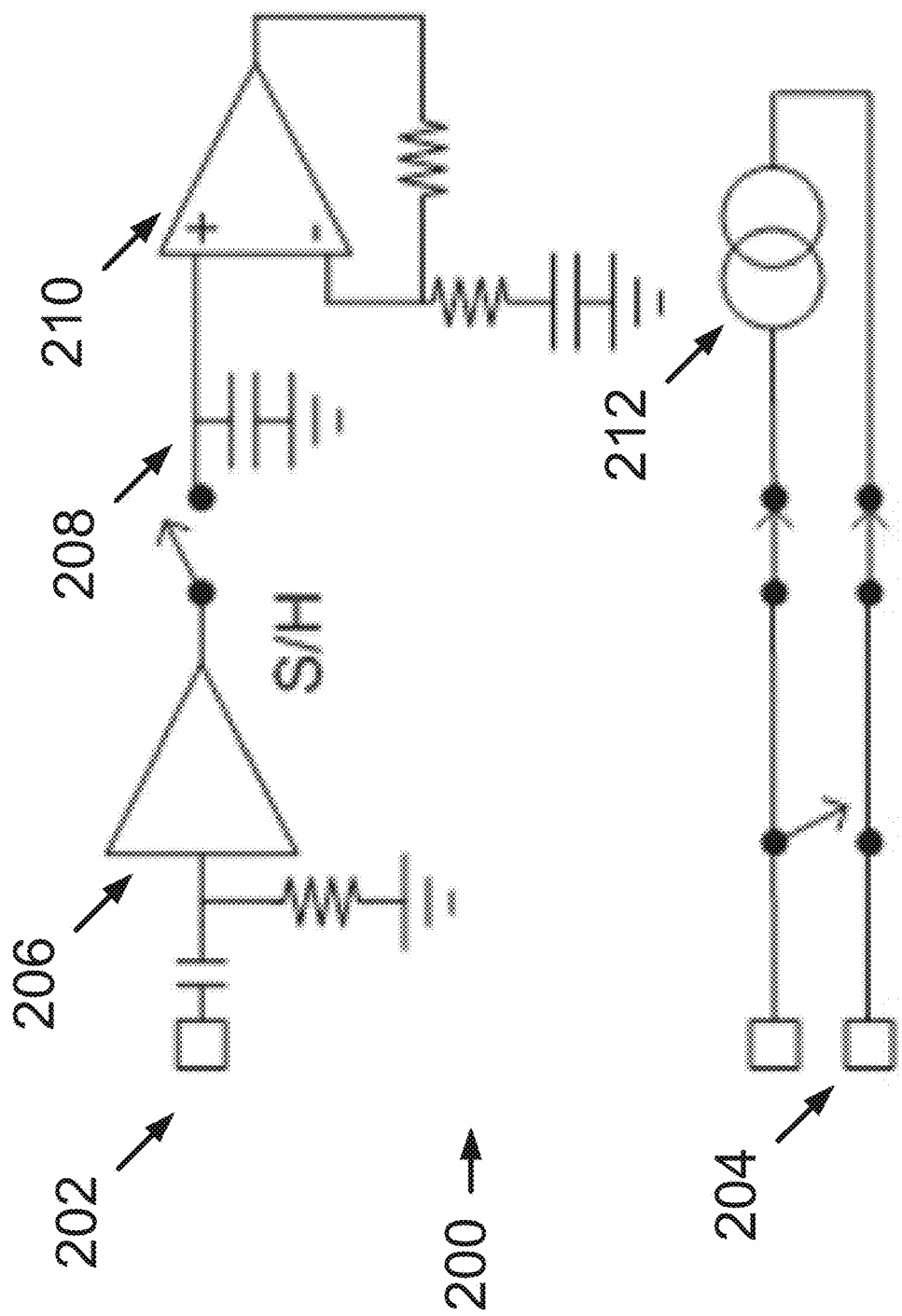
FIG. 2C illustrates the circuitry of one embodiment of the present invention during the stimulate phase of a measurement cycle.

In the third phase shown in FIG. 2C, the stimulation is applied. The stimulus electrodes 204 are switched to the current source 212, and the sample-and-hold 208 is set to "hold" so that the large stimulus crosstalk seen on electrode 202 is not presented to the measurement amplifier 210.

Figure 2D:
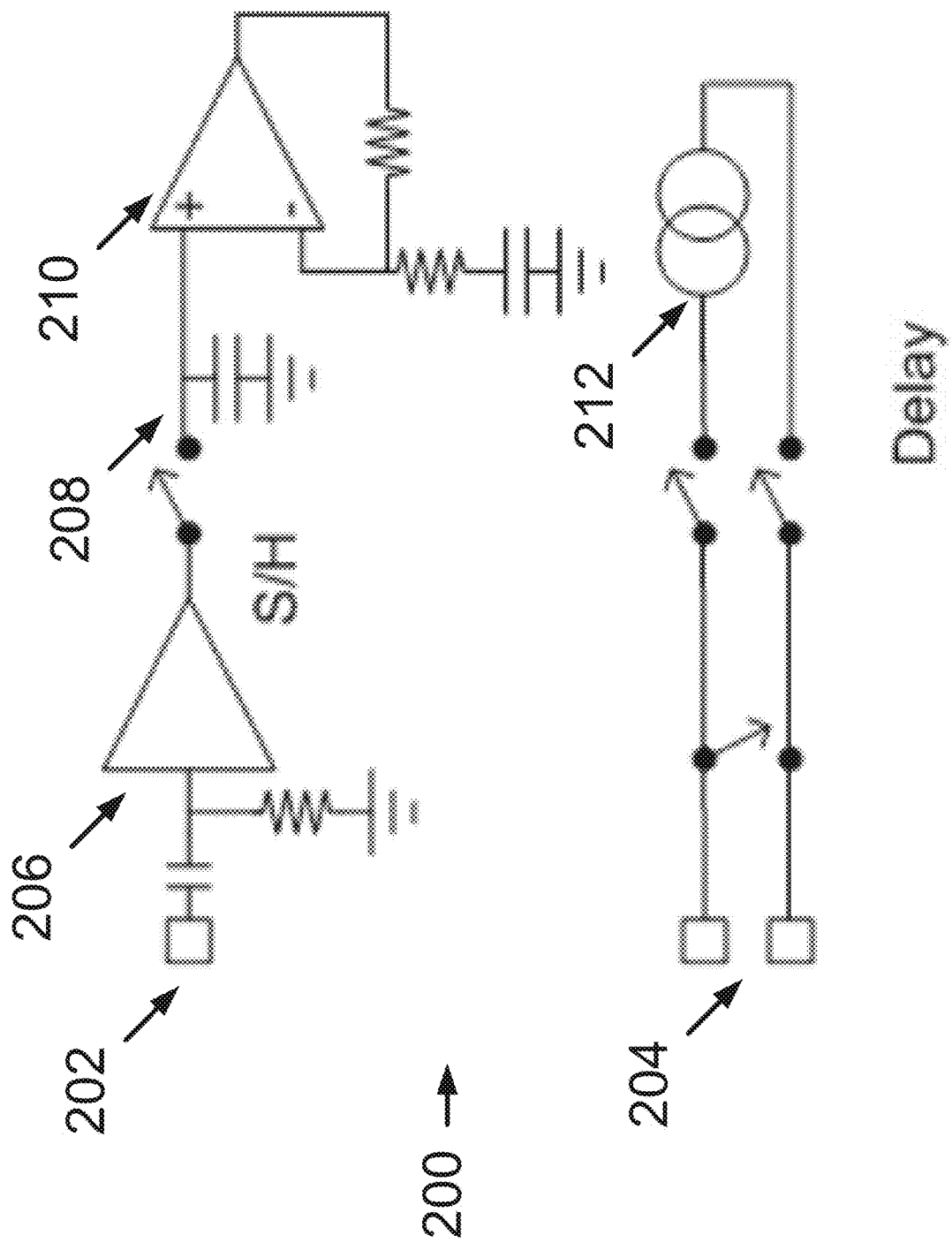
FIG. 2D illustrates the circuitry of one embodiment of the present invention during the delay phase of a measurement cycle.

The fourth phase shown in FIG. 2D provides for a post-stimulus delay. In this phase the stimulus electrodes 204 are open circuited, and the sample-and-hold remains in the "hold" position, to allow the electrodes 202, 204 settle towards equilibrium, as defined by bio-electrical conditions.

Figure 2E:
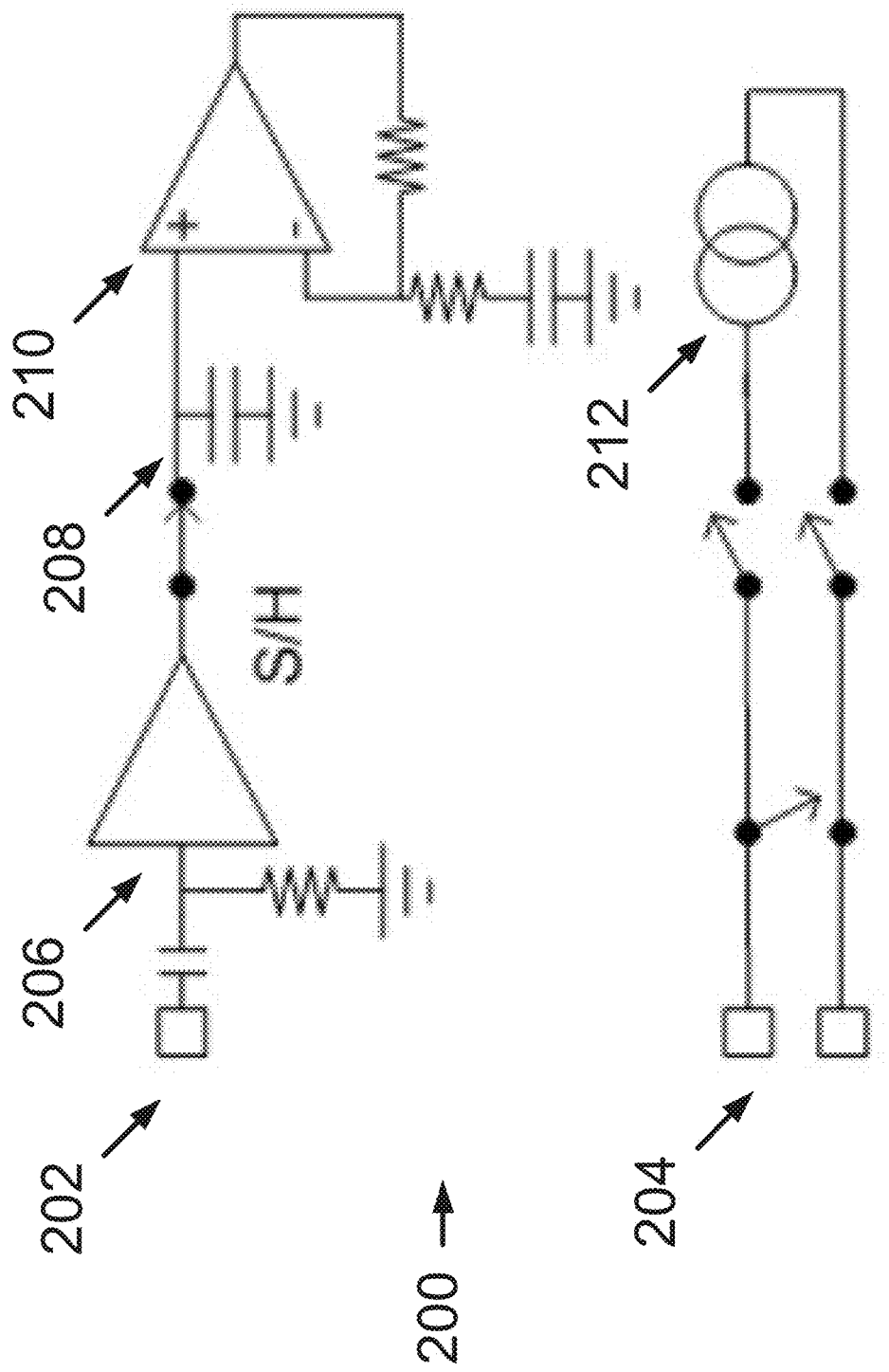
FIG. 2E illustrates the circuitry of one embodiment of the present invention during the measure phase of a measurement cycle.

Finally, in the fifth phase shown in FIG. 2E, the SCP present at sense electrode 202 is measured by switching the sample-hold 208 to "sample".

When performing repeated measurement cycles in this fashion, it is noted that the switch positions are the same in the phase 1 "settling" and the phase 5 "measuring" states. Thus, the state of phase 5 is maintained, by virtue of a subsequent phase 1, until the electrodes and circuitry are in equilibrium, even after the time that useful SCP data is no longer present or being captured. Such embodiments thus provide a greater length of the "settle" state.

Figure 3:
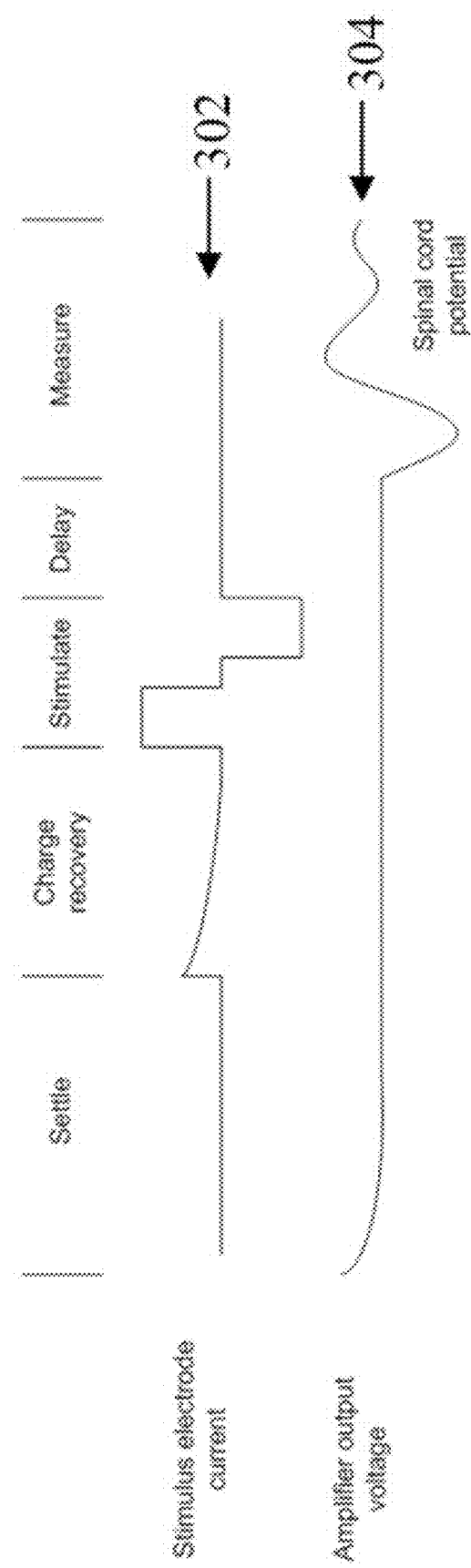
FIG. 3 illustrates idealised waveforms arising in the circuit of FIG. 2 during each phase of the measurement cycle.

FIG. 3 shows idealised waveforms arising during the SCP measurement process of FIG. 2. FIG. 3 illustrates the current 302 of stimulus electrodes 204, and the output voltage 304 of amplifier 210, during each of the five phases of the measurement cycle. Importantly, it can be seen that phase 1 permits the amplifier bias point to settle to a steady state as defined by bio-electrical conditions at the sense electrode, while phases 2-4 do not disrupt the amplifier 210 bias point.

An advantage of this circuit is that in the phase 2 equilibration, the circuitry around amplifier 210 is a low-pass filter, and is therefore relatively immune to noise and input transients. This also allows the amplifier 210 to accumulate its bias point over successive measurement cycles, as it does not need to be reset for each cycle. Moreover, because of the buffer 206 before the sample/hold 208, the input-referred effect (i.e. the effect upon sense electrode 202) of the charge injection into the sample/hold 208 is lower.

In the embodiment of FIG. 2, the sense electrode 202 is never shorted to the stimulus electrodes 204, recognising that this creates dis-equilibrium in the sense electrodes and adds artefact, rather than having the effect of creating equilibrium as previously thought. In some embodiments, it may be possible to overlap the "settle" (equilibrate) phase of FIG. 2A, and the "charge recovery" phase of FIG. 2B, although it would be expected that the artefact would be higher, and the time taken to reach equilibrium longer.

Figure 4:
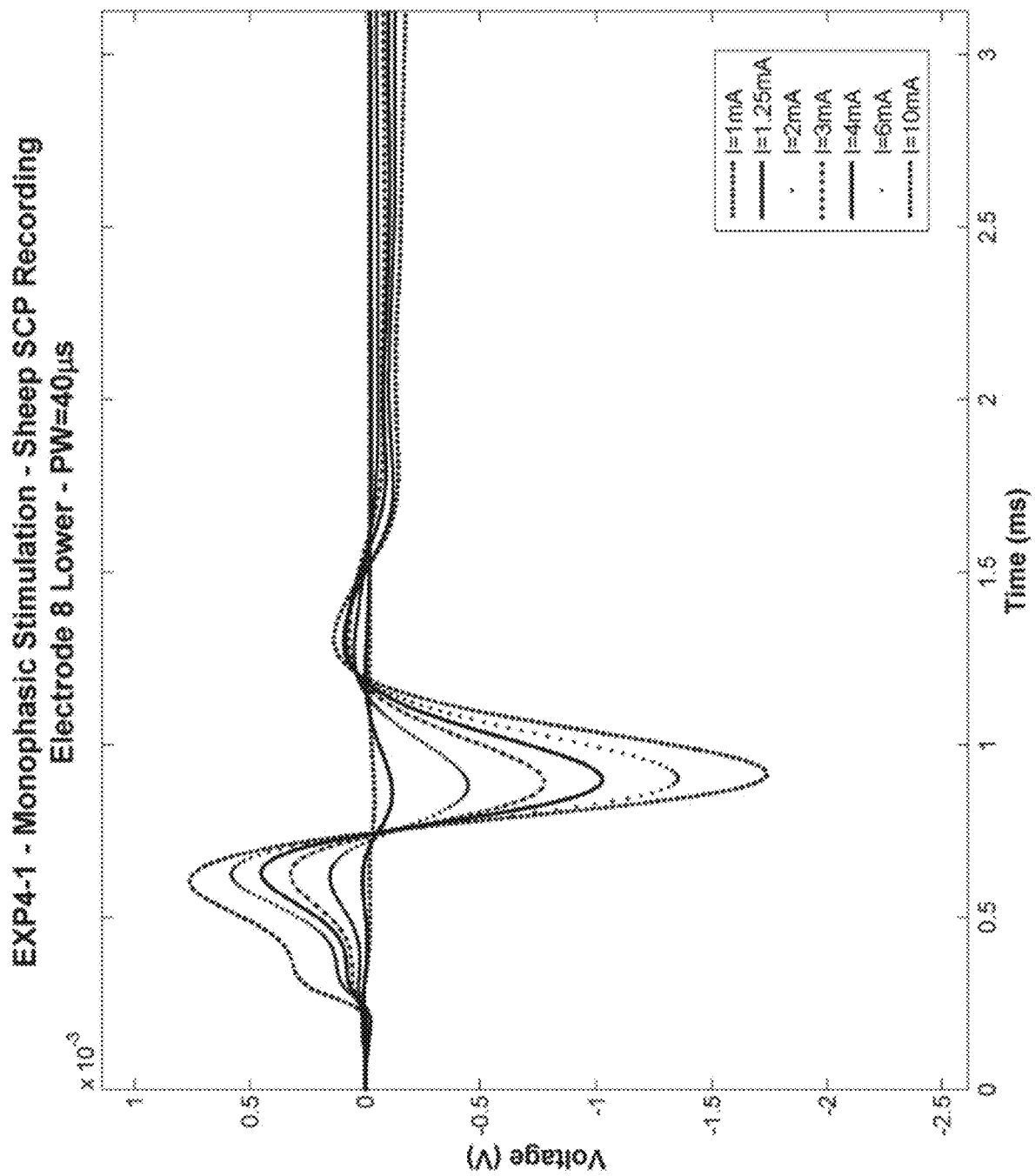
FIG. 4 illustrates SCP measurements made using the embodiment of FIG. 2.

FIG. 4 is a plot of 22 separate measurements of ovine SCP made using the embodiment of FIG. 2. The measurements were obtained sequentially for differing stimuli, the stimuli comprising biphasic current pulses of 40 µs pulse width and a current amplitude which varied from 0-10 mA. The measurements were then plotted on a single chart to produce FIG. 4. The recorded signals consist of the neural response and a small electrode artefact. The neural response is tri-phasic, consisting of a positive P1 peak followed by a negative N1 peak and then a secondary positive P2 peak. The neural response morphology in FIG. 4 is characteristic of extracellular recordings of axonal compound action potentials. The first phase P1 is dominated by the capacitive current due to the initial membrane depolarization. Phase 2 is dominated by $Na^+$ ion current and is negative due to the influx of $Na^+$ ions during the neuronal membrane action potential. The third phase is positive due to the $K^+$ ion conduction during repolarization.

The waveforms of FIG. 4 have lower dynamic range and simpler morphology than measurements produced by previous approaches, due to the absence of stimulus crosstalk and reduced artefact. When wishing to provide a system built on an implanted integrated circuit, wide dynamic range amplifiers are difficult to design, as are signal processing systems for feature extraction. Beneficially, the nature of the measured waveforms shown in FIG. 4 permits, for example, a circuit for extracting the peak-to-peak SCP amplitude to have fewer components than would be required to operate upon the waveform produced by previous approaches. Thus the techniques of the present invention for artefact reduction greatly assist in building a practical implanted, evoked response feedback system.

Moreover, it is notable that in this case of a 40 μs pulse width the measurement system is settled and ready to record prior to onset of the evoked CAP. The sense electrode was less than 50 mm from the stimulus electrode, and a post-stimulus delay of 50 μs was observed before the measurement amplifier was switched in to obtain the recordings shown in FIG. 4. As can be seen in FIG. 4 the largest peak to peak response was about 2.4 mV, significantly less than the voltage present when applying a 10 mA stimulus. Moreover, the epidural space is much smaller in sheep than in humans, and so the electrode is expected to be closer to the ovine neural tissue and the magnitude of the sensed tri-phasic potentials is correspondingly higher in the sheep than is expected for humans, emphasizing the difficulty of making such recordings.

Figure 5:
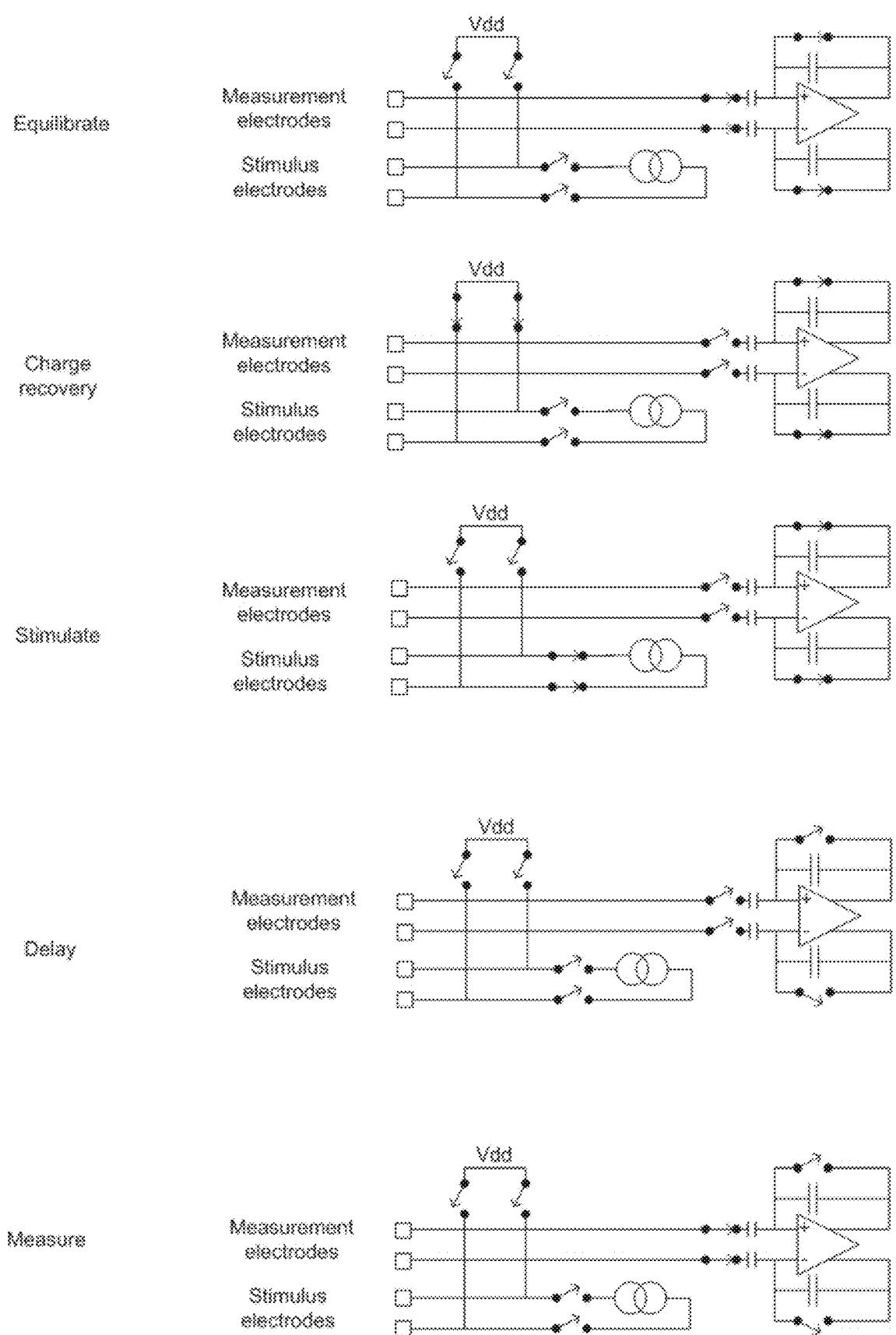
FIG. 5 illustrates the circuitry of an alternative embodiment of the invention implementing differential CAP measurements.

FIG. 5 illustrates the circuitry of an alternative embodiment of the invention in which a differential measurement amplifier is used, and charge recovery is via a voltage rail $V_{dd}$. As can be seen, in accordance with the present invention the measurement phases are carried out in a corresponding manner despite the use of different hardware.

Figure 6:
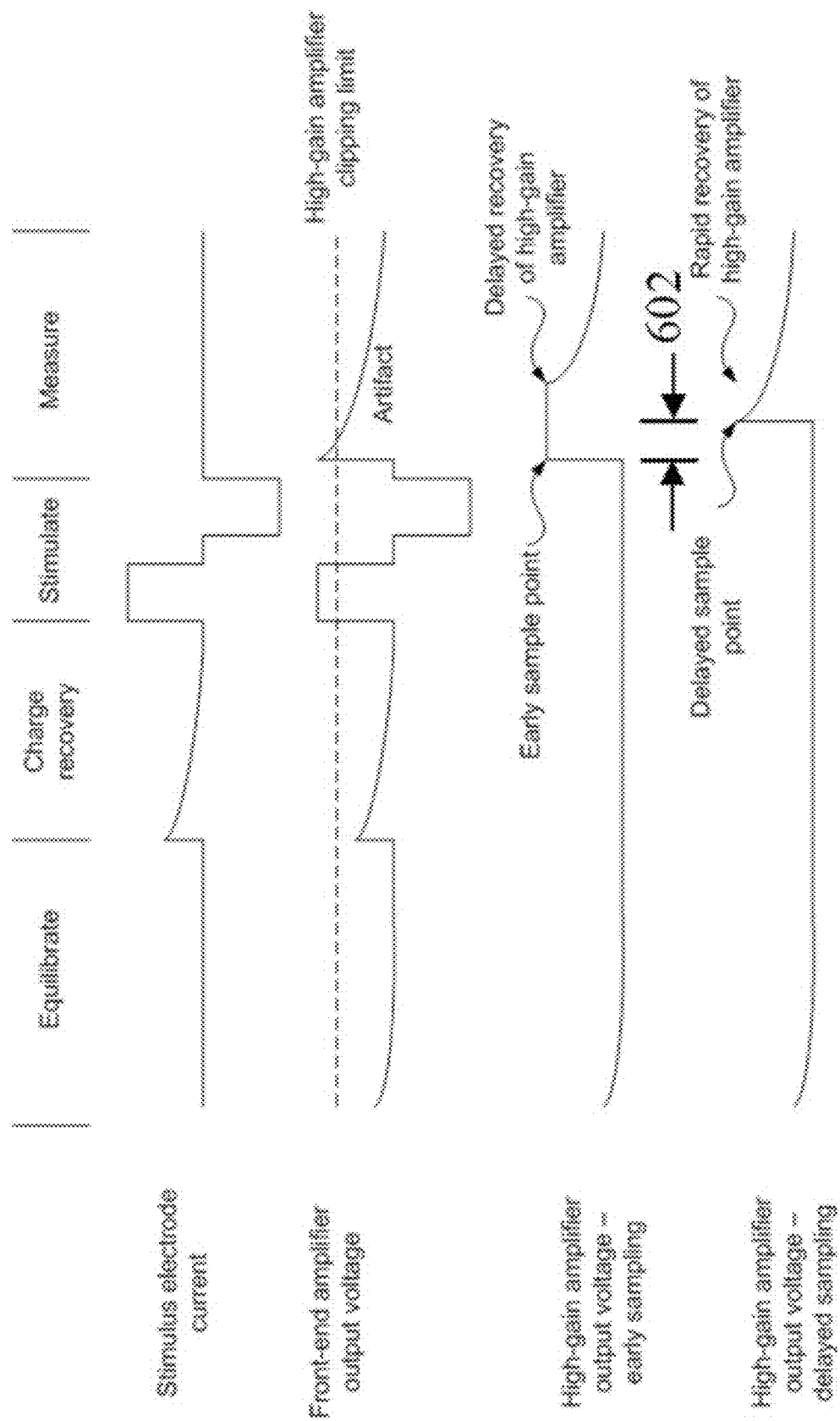
FIG. 6 illustrates delayed activation of a measurement amplifier to avoid clipping.

In the embodiments of either FIG. 2 or FIG. 5, artefact can cause the high-gain measurement amplifier 210 to clip, and the amplifier can subsequently be slow to recover. However, in preferred embodiments the sample point, being the transition from the "stimulate" to "measure" phases, is delayed, allowing clipping to be avoided. FIG. 6 illustrates the manner of determining a suitable delay 602, which is often in the range of 50-200 μs, noting that the fast response typically concludes within about 2 ms. Such embodiments may permit use of a higher amplifier gain than would otherwise be the case. In particular, a variable delay and increased amplifier gain may be particularly apt in circumstances where high-gain is desired, and parts of the SCP of interest do not immediately follow the stimulation. Thus, delaying the start of measurement will avoid the side effects of clipping.

Figure 7:
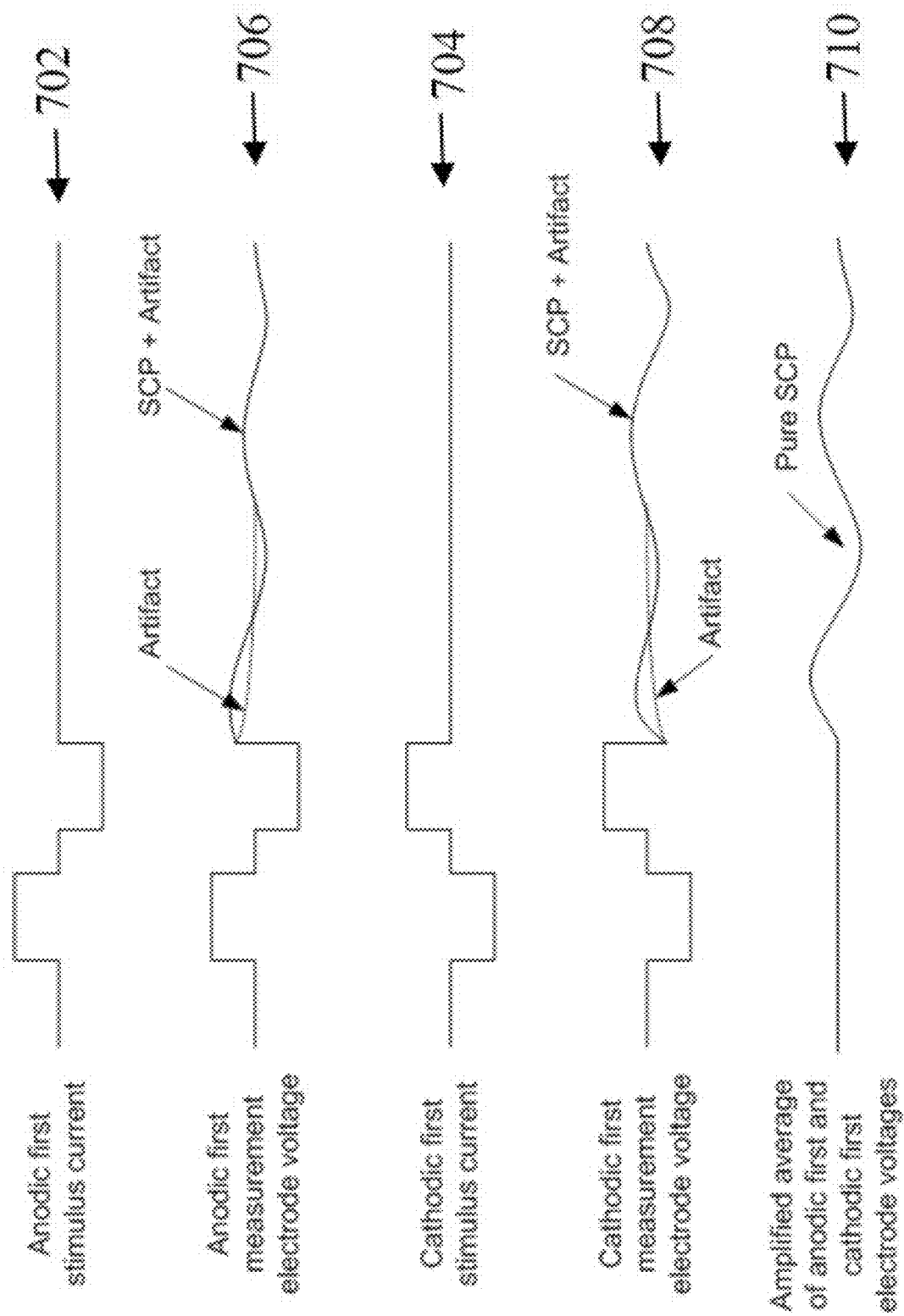
FIG. 7 illustrates an embodiment in which alternate phased stimuli are used to obtain an averaged CAP measurement.

In another embodiment of the invention shown in FIG. 7, a method to eliminate artefact from an SCP measurement is to alternate the phase of stimulus waveforms and take an average of obtained measurements. This method is effective when the stimulus electrodes have different area. For example, in tripolar stimulation a central electrode is driven anodically in the first phase and consists of a single electrode of the array, whereas the electrode driven cathodically in the first phase consists of two electrodes of the array connected in parallel. The electrodes in parallel would usually be on either side of the other stimulating electrode. Similarly, if stimulation were between one electrode in the epidural space and one electrode elsewhere, such as being attached to an implant body, then a mode of stimulation referred to as "monopolar" stimulation is obtained.

FIG. 7 shows the stimulus current for a positive "anodic-first" stimulus 702, and the stimulus current for a negative "cathodic first" stimulus 704. In this embodiment these are applied in succession with respective CAP measurements obtained after each stimulus. The respective measurement electrode voltages 706 and 708 arising from each such stimulus are also shown. It will be observed where indicated in waveforms 706, 708 that the artefacts from each of the two stimuli are of substantially identical magnitude, but opposite sign. In most situations it will be found that the artefact polarity depends on the stimulus polarity. An example of this would be electrical artefact caused by the high-pass poles of the front-end amplifier 206. Clearly, either phase could be used for stimulating nervous tissue, though their effects will differ.

In contrast, the positive and negative phase stimuli 702, 704 produce SCPs of differing amplitudes, but approximately similar shape and importantly of similar polarity, as this is determined by the anatomy and physiology of the spinal cord nerve fibre membranes. Thus, when the voltages 706, 708 resulting from the positive and negative phase stimuli 702, 704 are recorded, and averaged, the opposite phase stimulation artefacts substantially cancel, leaving the SCP or a combination of the two SCPs 710. Note that in practical situations, the artefact can have much higher amplitude than the SCP, making it much harder to detect the SCP than is apparent from FIG. 7.

The response of the spinal cord to these two polarities of stimulation are referred to as the "anodic" and "cathodic" SCP responses, as referred to the electrode considered to be that closest to the recording electrode. I.e. anodic tripolar stimulation makes the central stimulating electrode anodic in the first phase of stimulus. Usually cathodic stimulation has a lower threshold for neural activation than is the case for anodic stimulation. Nevertheless, the SCP polarity is independent of whether the stimulus is anodic 702 or cathodic 704.

Figure 8A:
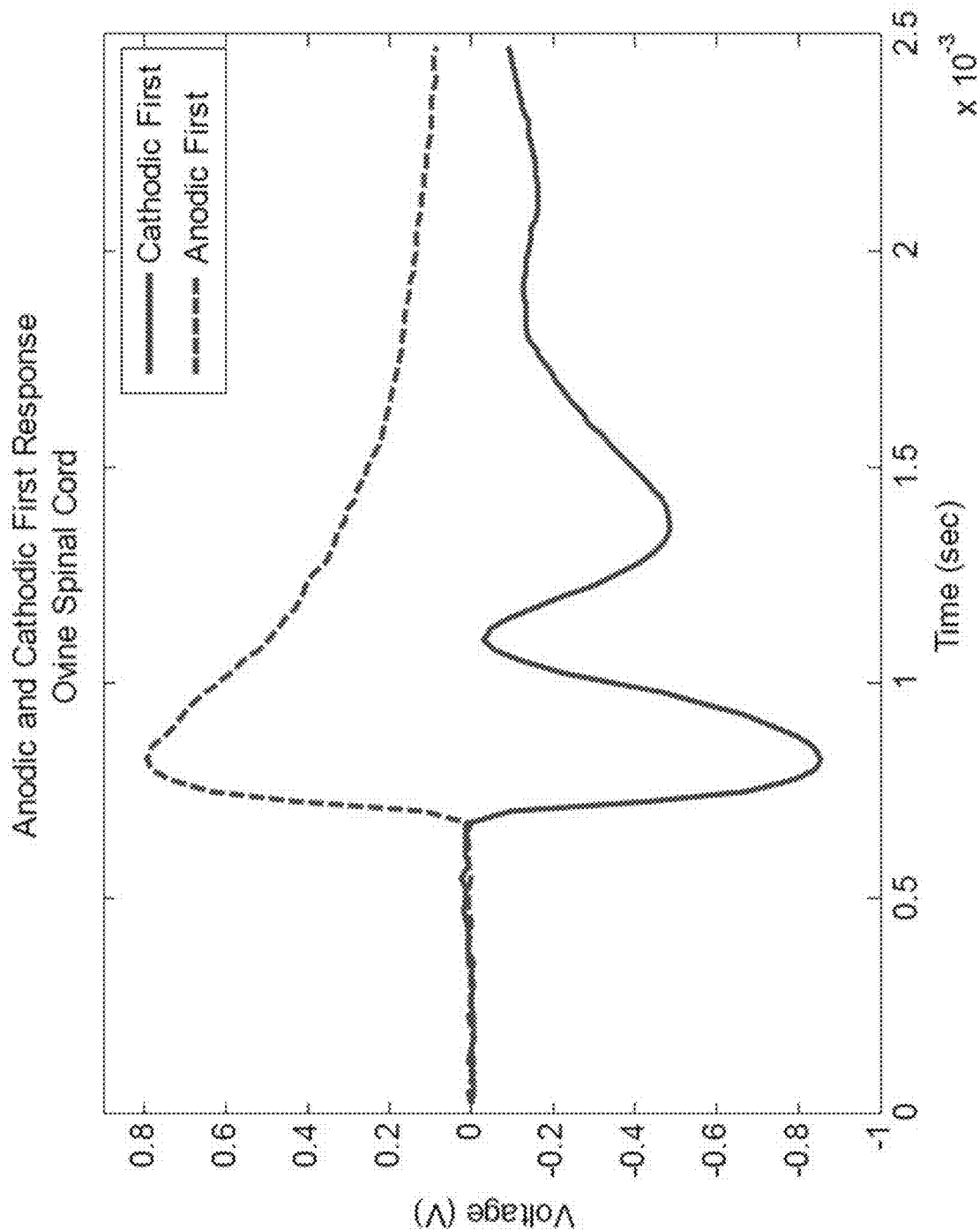
FIG. 8a illustrates the "anodic first" and "cathodic first" CAP responses induced by the method of FIG. 7.

FIG. 8a illustrates spinal cord measurements obtained in response to anodic and cathodic monophasic stimulations, respectively, the stimuli being of equal amplitude. Note that the measurement obtained in response to the anodic stimulation lacks the characteristic P1-N1-P2 form, indicating that the anodic stimulation did not evoke a neural response in this case. In contrast, the measurement obtained in response to the cathodic stimulus exhibits a significant evoked neural response.

Figure 8B:
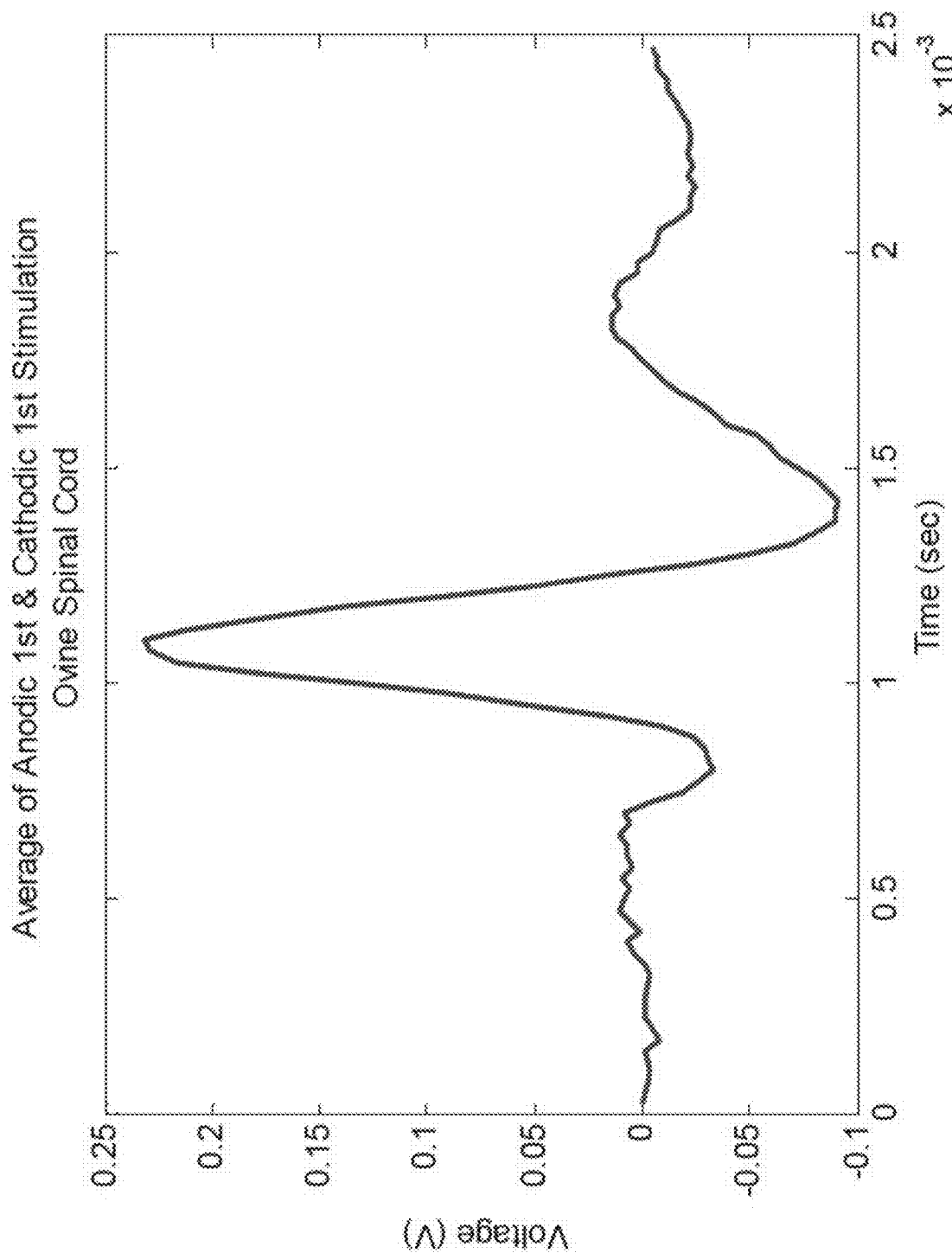
FIG. 8b illustrates the averaged measurement obtained by the method of FIG. 7.

FIG. 8b shows an average of the two responses in FIG. 10a. As can be seen, while the characteristic form of the SCP has been altered, the artefact is essentially removed as stimuli of opposite polarity and equal amplitude produce artefact of opposite polarity and equal amplitude, which cancel when averaged.

Figure 9:
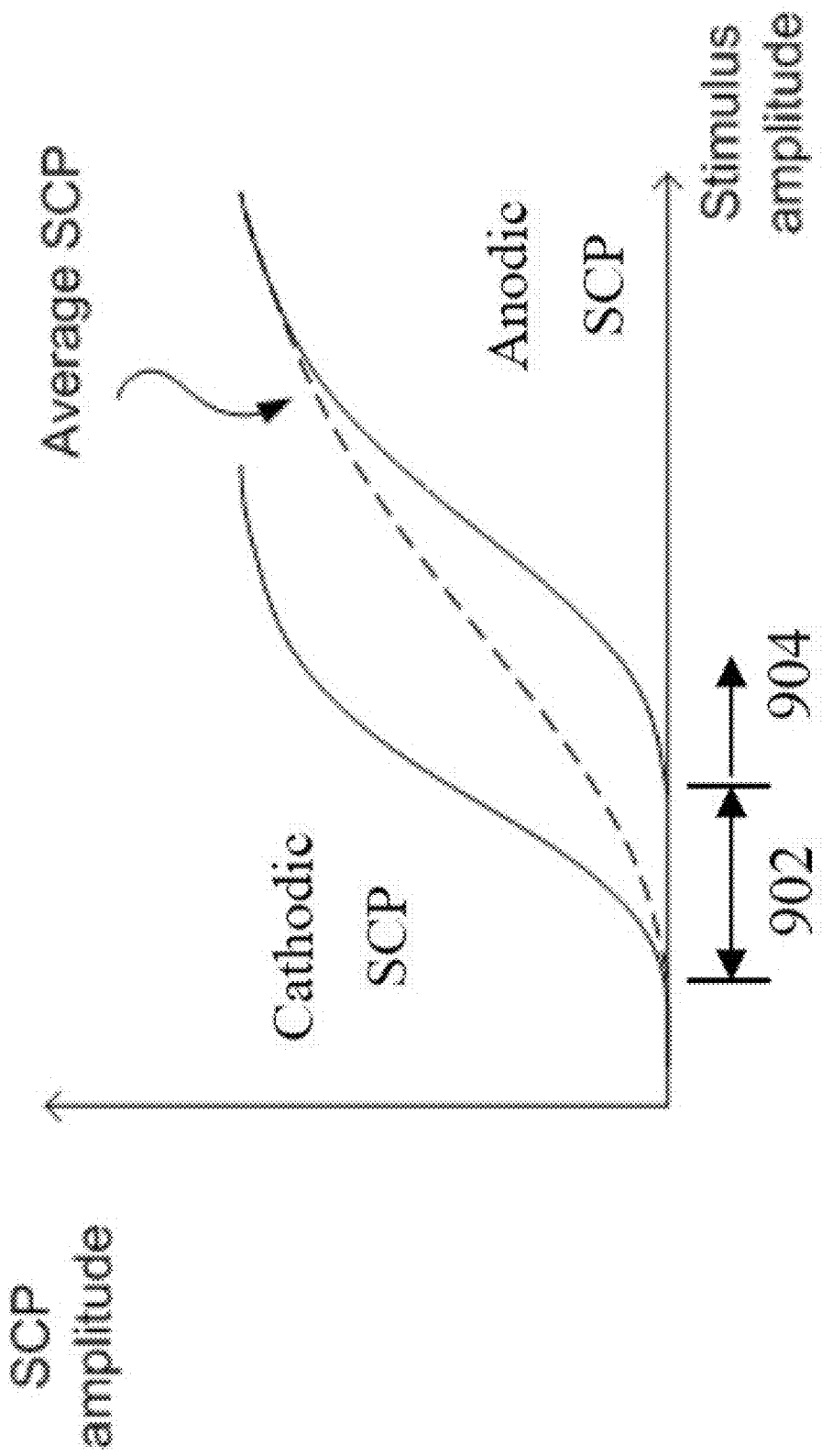
FIG. 9 illustrates the CAP response to anodic-first and cathodic-first stimuli, respectively, with increasing stimulus amplitude.

This embodiment of the invention further recognises that the averaged waveform of FIG. 8b can be used to obtain a range of information despite the atypical SCP form. In this regard, FIG. 9 illustrates SCP growth curves against stimulus amplitude, for both anodic and cathodic monophasic stimuli. FIG. 9 also shows the growth behaviour of the average SCP against stimulus amplitude. It can be seen from FIG. 9 that the threshold of the average response is identical to the threshold of the more sensitive response for cathodic stimulation.

When the stimulus amplitude is in the range 902 such that only the cathodic stimulus produces an SCP, then the averaged SCP waveform would have a normal SCP morphology but would be half the amplitude compared to a true cathodic SCP due to the averaging. In the region 904 where both the anodic and cathodic responses contribute to the averaged SCP, the resultant averaged SCP waveform will have morphology in between the two measurements. It would not directly represent an SCP, but rather the average of two different SCPs. Nevertheless, this waveform could still be valuable for example in implementing an automatic control loop for stimulation adjustment, as it gives a value proportional to neural recruitment.

It is further to be noted that the principle portrayed by FIG. 9 applies in a similar manner to other stimulus polarities. For example, some embodiments may stimulate with a tripolar arrangement having a centre electrode operating as a cathode and having two edge electrodes, being those immediately to each side of the centre electrode, operating as anodes. This tripolar arrangement means that the recovery charge is shared between the two edge electrodes. For a biphasic tripolar stimulus the cathodic charge on the 2nd phase is shared between two electrodes and thus is half that on the first phase. Thus the principle shown in FIG. 9 is true for tripolar stimulation, at least up to the point where the current is twice the threshold current at which point the edge electrodes' currents are each at the threshold and will thus start to generate action potentials.

Some embodiments of the invention, such as the embodiment of FIG. 5, may use differential amplifiers so as to detect the voltage difference between two sense electrodes. Differential amplifiers simplify the task of separating electrode artefact. If they are connected to electrodes with similar area, and separated from the stimulation electrodes in a similar manner, then they receive similar levels of electrode artefact and this will be removed when their difference voltage is obtained. However, in such a system the voltage recorded by the amplifier is the difference between the voltages at two points along a bundle of neurons, and can thus be difficult to interpret. When making SCP measurements, it is preferable to use single-ended amplifiers as they more accurately measure the SCP, and they are more sensitive in measuring the SCP.

Figure 10:
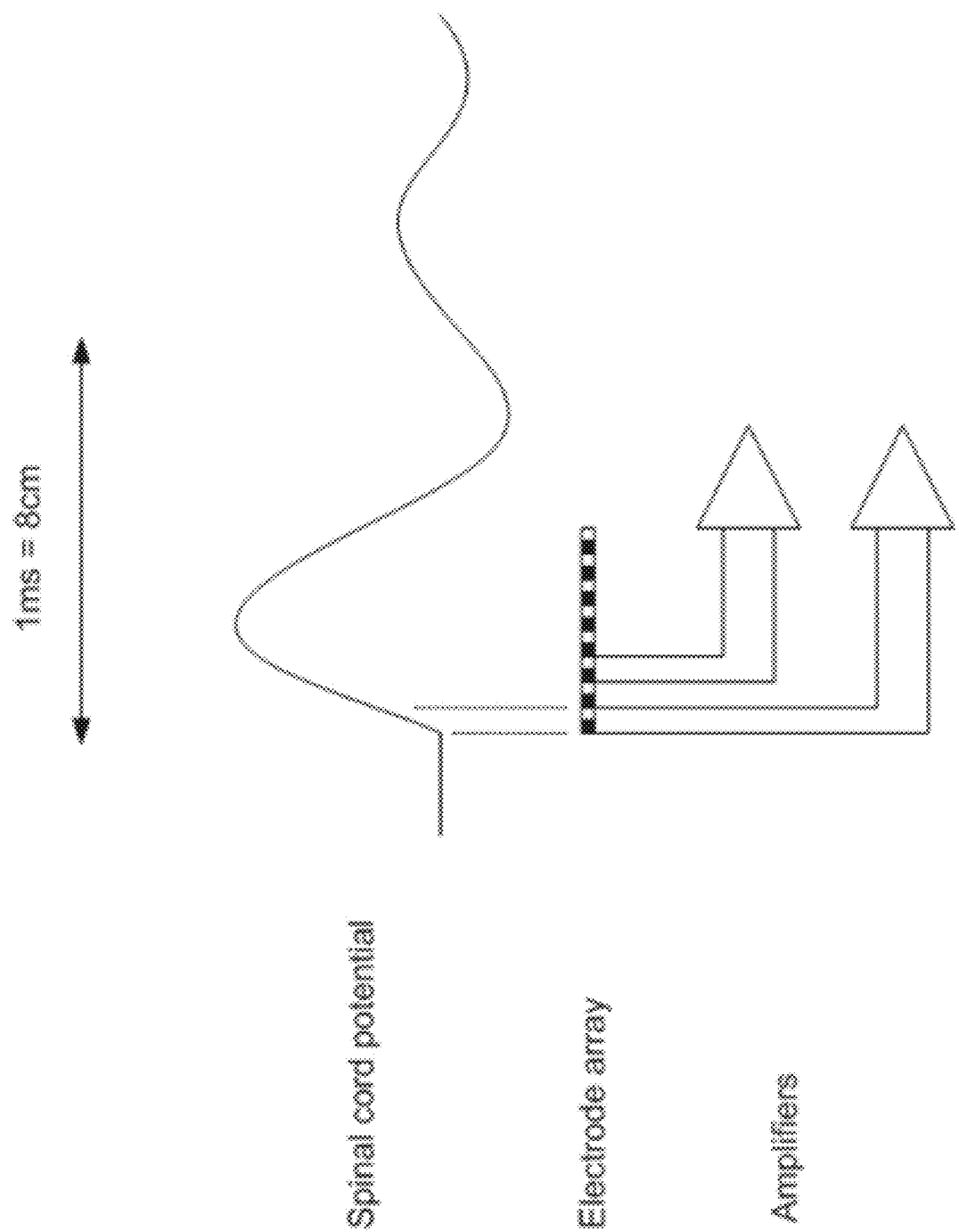
FIG. 10 illustrates the nature of differential CAP measurements in the spinal cord.

Differential amplifiers are often used because they provide a means to reduce electrode artefact, when other means have been insufficient. However, FIG. 10 illustrates a problem of measuring SCPs with differential amplifiers. It shows a spinal cord potential. As this potential travels along the spine at a velocity, which can be as high as 80 m·s$^{-1}$, it can also be considered as a spatial wave. Given that a peak-to-peak cycle of the fast response of an SCP typically lasts for 1 ms, the wave will travel 8 cm in this time. Using this 1 ms=8 cm scale, a 5 cm electrode array is drawn alongside the SCP in FIG. 10. Connected to this electrode array are two amplifiers configured to make differential SCP measurements from separate pairs of sense electrodes. As can be seen from FIG. 10, the difference between the voltages on the adjacent electrodes will be quite small and significantly smaller than the peak to peak amplitude of the SCP, and thus more susceptible to electrical noise generated by the amplifier. The output of the amplifier will approximate the differential of the SCP, and thus be harder to interpret than a simple measure of the SCP itself. If measuring evoked SCPs with a micro-package stimulator design, for example in a system using a two-wire bus, differential measurements between non-adjacent electrodes are not possible. Further, if wishing to measure the slow response of the SCP, which has a period of about 6 ms and correspondingly reduced signal gradients, differential measurements are even more difficult to effect. Thus it will be appreciated that single-ended measurements are preferable, as long as artefact can be kept at a sufficiently low level.

With the measurement sequence of the present invention, the artefact is reduced so that some embodiments may instead use a single-ended amplifier, even in situations where previously they would have suffered from too much electrode artefact. Moreover, trials to date show that recording can be initiated with an extremely short time interval from cessation of the stimulus, permitting the same electrode array to be used for recording and stimulation, and even permitting recordings to be made on the electrode immediately adjacent to the stimulus electrode in an electrode array with electrode spacings of less than 10 mm.

Single ended amplifiers have the further advantage that they consist of fewer capacitors and amplifier components than differential amplifiers, so will take up less space on a silicon chip, which is a significant benefit when intended for use in an implanted system with many electrodes and where the silicon area for each amplifier is limited.

Preferred embodiments of the invention may comprise a separate amplifier chain (e.g. 206, 208, 210, see FIG. 2) for every electrode, organised in parallel manner, permitting simultaneous recording of a single CAP from multiple sense electrodes in parallel, and also eliminating the switching noise arising in systems which switch the sense electrode to a shared measurement amplifier.

Figure 11A:
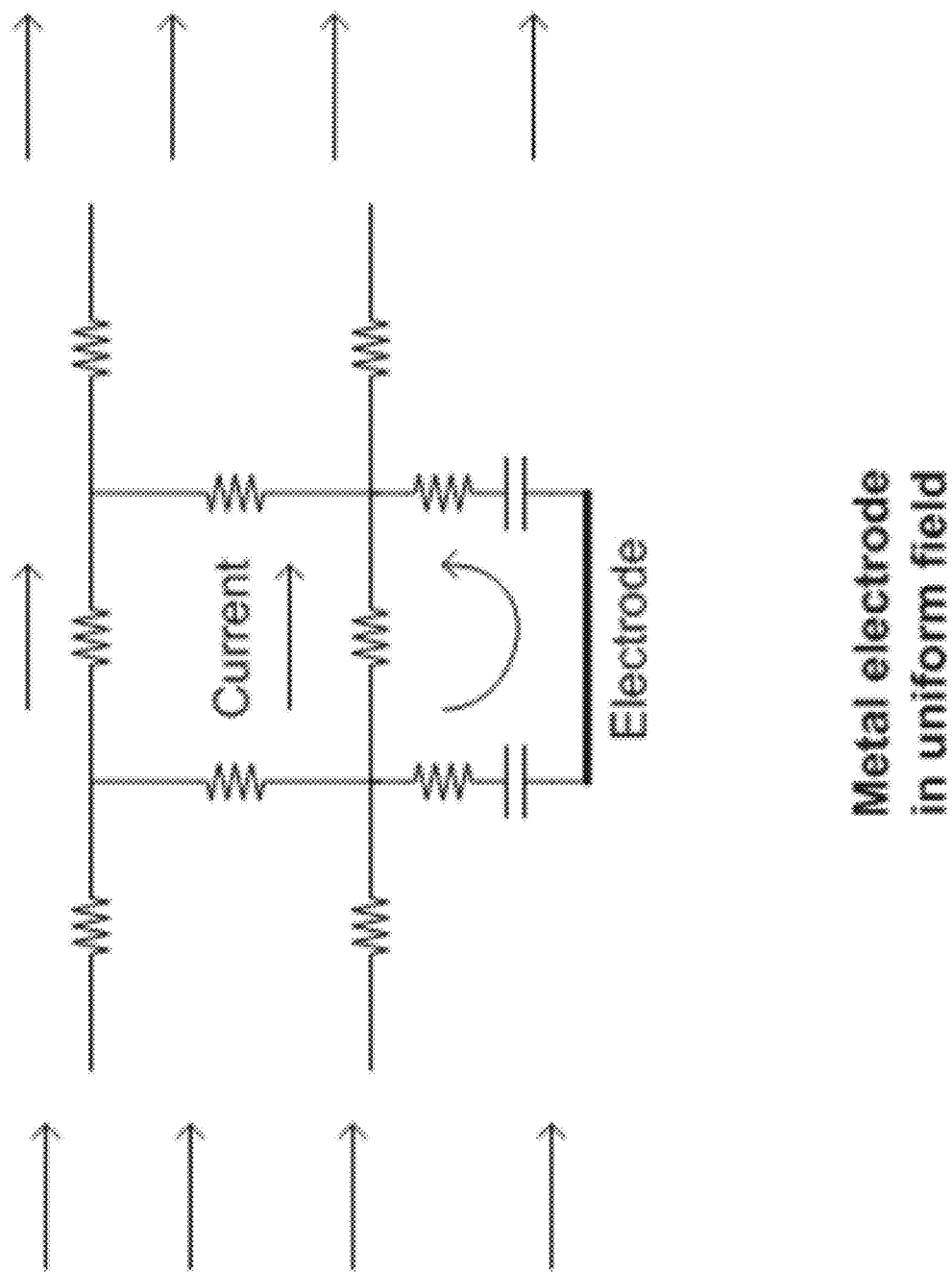
FIG. 11A illustrates a model of a metal electrode in a uniform electric field.

Further embodiments of the invention may employ divisible electrodes, as discussed below with reference to FIG. 11A, FIG. 11B, FIG. 11C, and FIG. 11D. When considering electrode artefact in particular, the sources of electrode artefact are relatively poorly understood. The surface of a metal electrode can be modelled as an RC network. For an accurate model, an infinite-phase element is required, but for the explanation of artefact a simple RC model will suffice, as shown in FIG. 11A. A conductive solution can be modelled as a mesh of resistors. Where a conductive solution meets a piece of metal of finite dimensions, the metal provides an alternative conduction path to the solution. This charges the electrode-to-tissue capacitances at the "ends" of the electrodes, with opposite polarities. The electrode does not acquire net charge, but it does cease to be in equilibrium. After the external current ceases, then the electrode will pass current through the solution as it re-equilibrates for a short time after the stimulus. This current will affect the potential of another electrode in the solution, and in the case of multi-electrode arrays a unique such current will arise at every electrode in response to local conditions experienced at that electrode. The cumulative impact of such re-equilibration currents is seen by a sense electrode as electrode artefact.

Figure 11B:
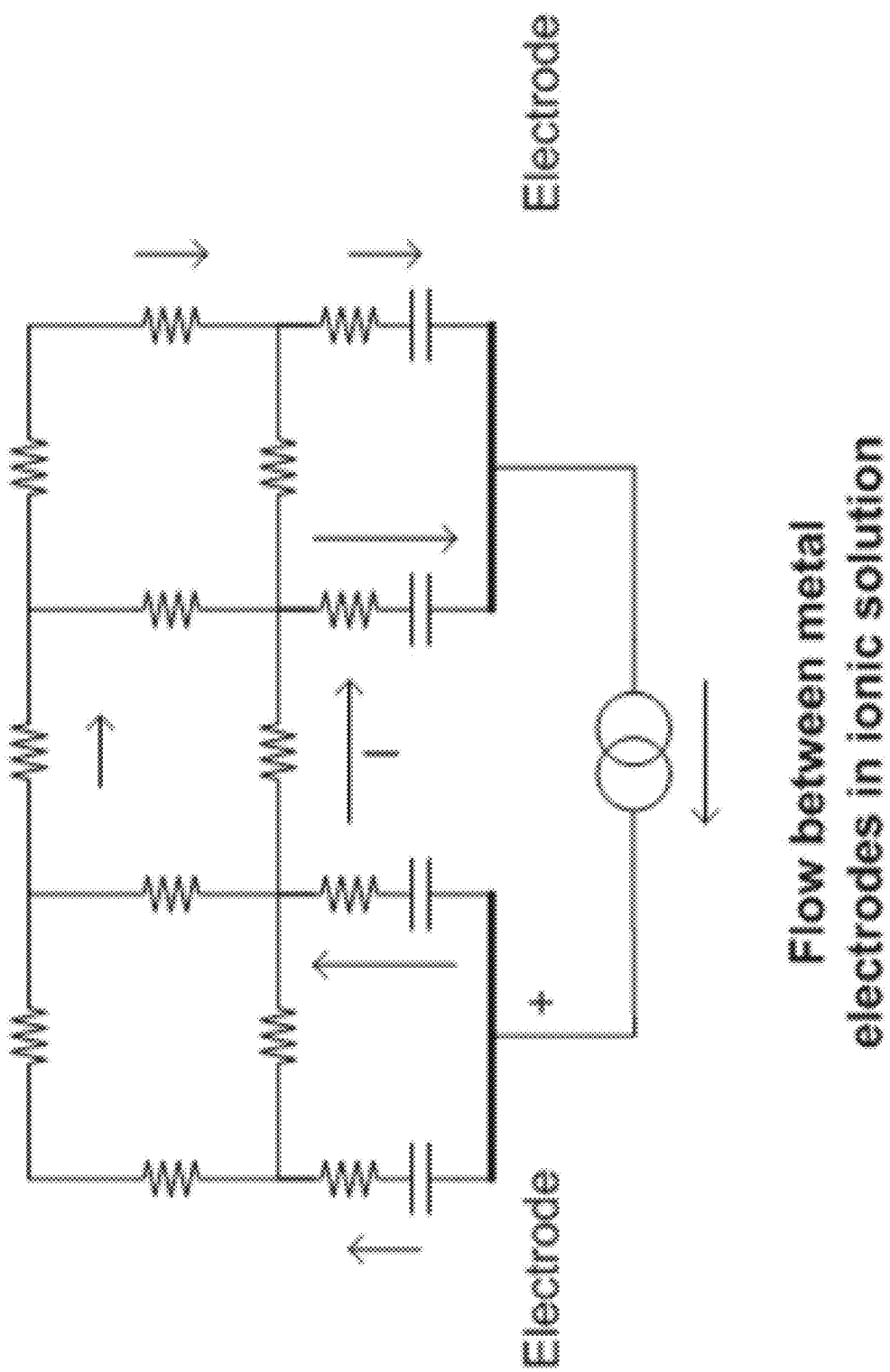
FIG. 11B illustrates a model of a metal electrode in a conductive solution.

A similar effect happens when current flows between two electrodes, as shown in FIG. 11B. During application of a stimulus, the current preferentially flows between the parts of the electrodes where they are closest. When the current is interrupted, the charge on the surface of the electrodes must re-equilibrate; this also leads to a residual current and contributes to electrode artefact seen by a sense electrode.

Figure 12A:
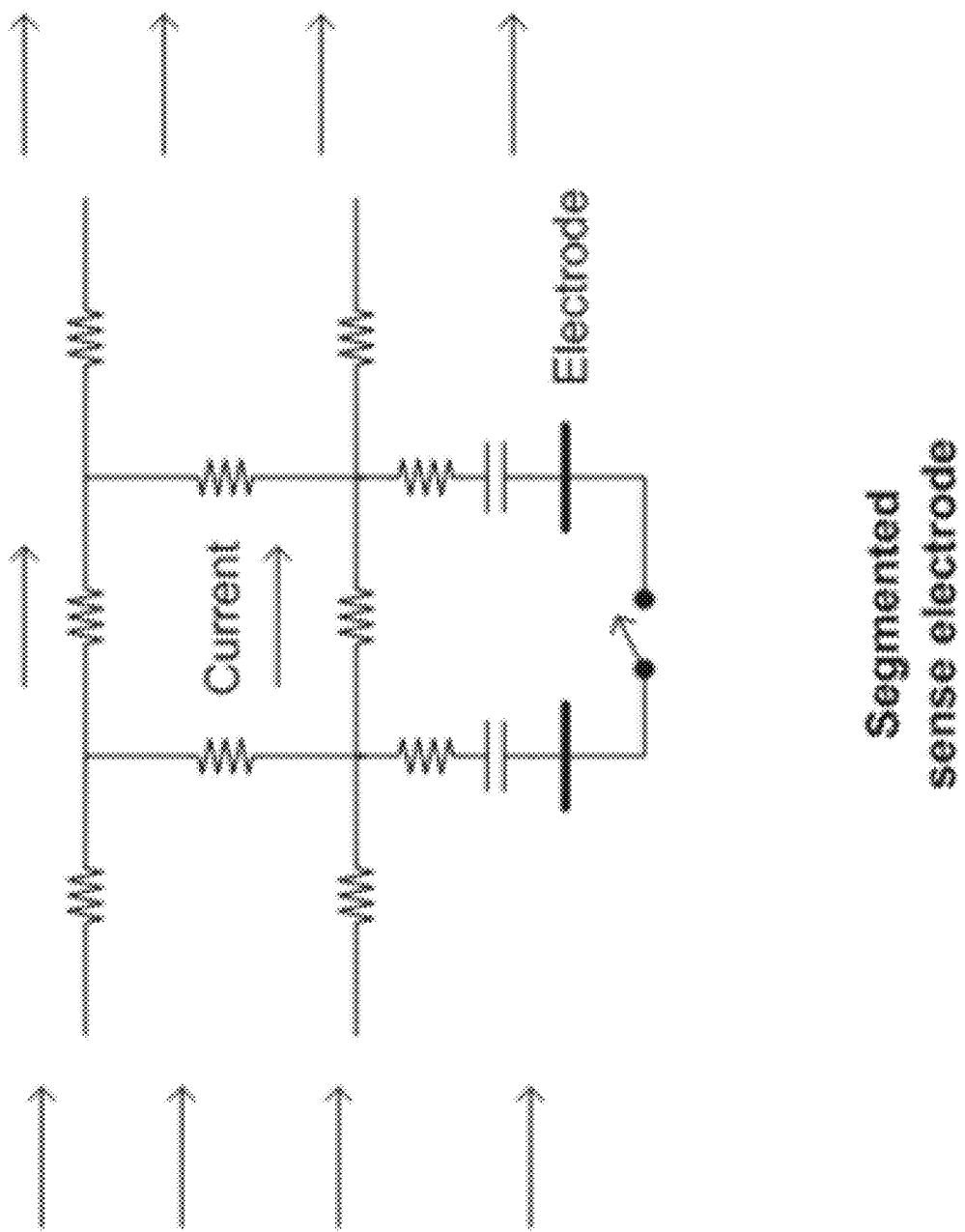
FIG. 12A illustrates segmented sense electrode which may be used to reduce artefact without sacrificing noise, impedance or current carrying capacity.
Figure 12B:
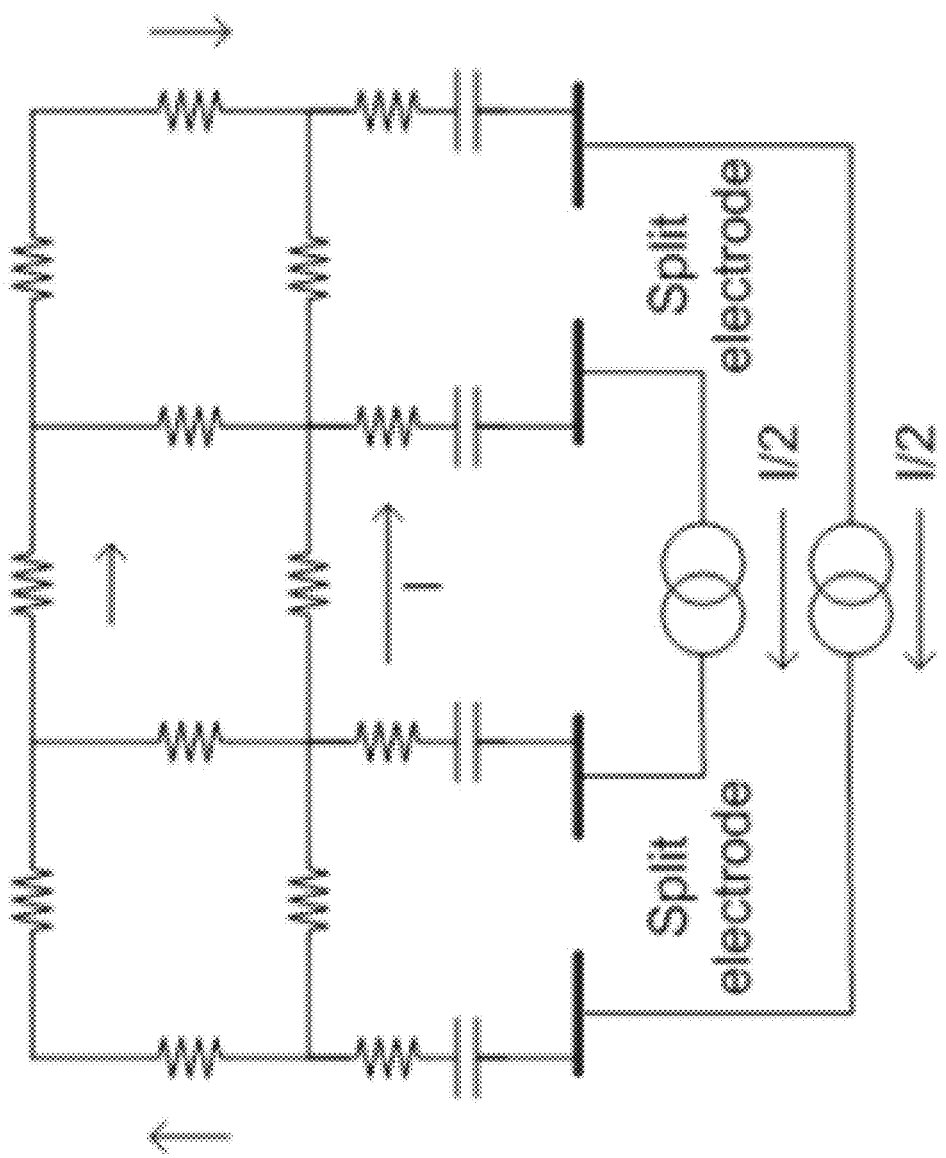
FIG. 12B illustrates a segmented drive electrode which may be used to reduce artefact without sacrificing noise, impedance or current carrying capacity.

The model of FIG. 11 predicts that using smaller electrodes will reduce artefact. However, smaller electrodes will have higher noise when used as measurement electrodes, and higher resistance and lower current carrying capacity when used as stimulus electrodes. Two means to reduce artefact without sacrificing noise, impedance or current carrying capacity are shown in FIG. 12A and FIG. 12B. The electrode configuration of FIG. 12A reduces artefact induced in a single metallic electrode; the electrode is composed of two or more smaller electrodes that can be disconnected during a stimulation phase, and reconnected during a measurement phase. In the configuration of FIG. 12B, an electrode is segmented, and individual current sources are provided for each segment. This forces the current in the segments to match, and so reduces artefact.

The evoked response telemetry of the present invention may in some embodiments be used to monitor the effect of a delivered compound. The administration of compounds (drugs or other chemical therapeutics) to effect a change in the nervous system is common for treatment of a wide number of diseases and disorders. Anaesthetics of various types are administered to the spinal cord for the relief of pain. Perhaps the most common form is administration of anaesthetics in the epidural space for pain relief during child birth.

In such embodiments, a catheter comprising a drug delivery tube may be fitted with electrode elements and configured to obtain neural response measurements in accordance with the present invention in order to monitor drug-induced effects on the neural response. Alternatively an electrode array may be temporarily or permanently implanted and used to apply neural stimuli and monitor the neural response. The neural response measurements may be obtained repeatedly during administration of the drug in order to directly measure the effect of the administered drug and control the dosage delivered.

Figure 13A:
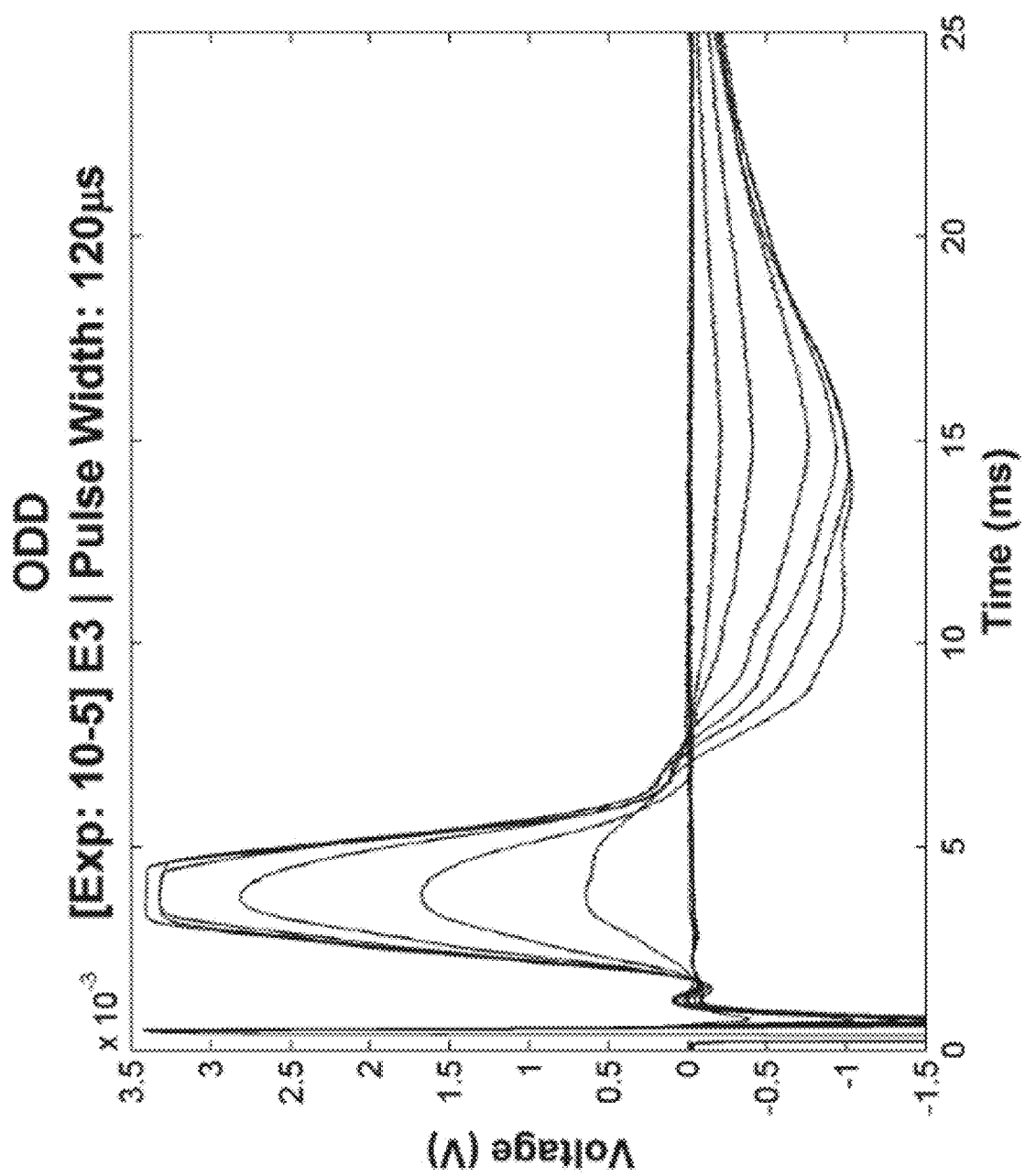
FIG. 13A and FIG. 13B illustrate the effect of epidural administration of Lignocaine on suppression of the spinal evoked responses.
Figure 13B:
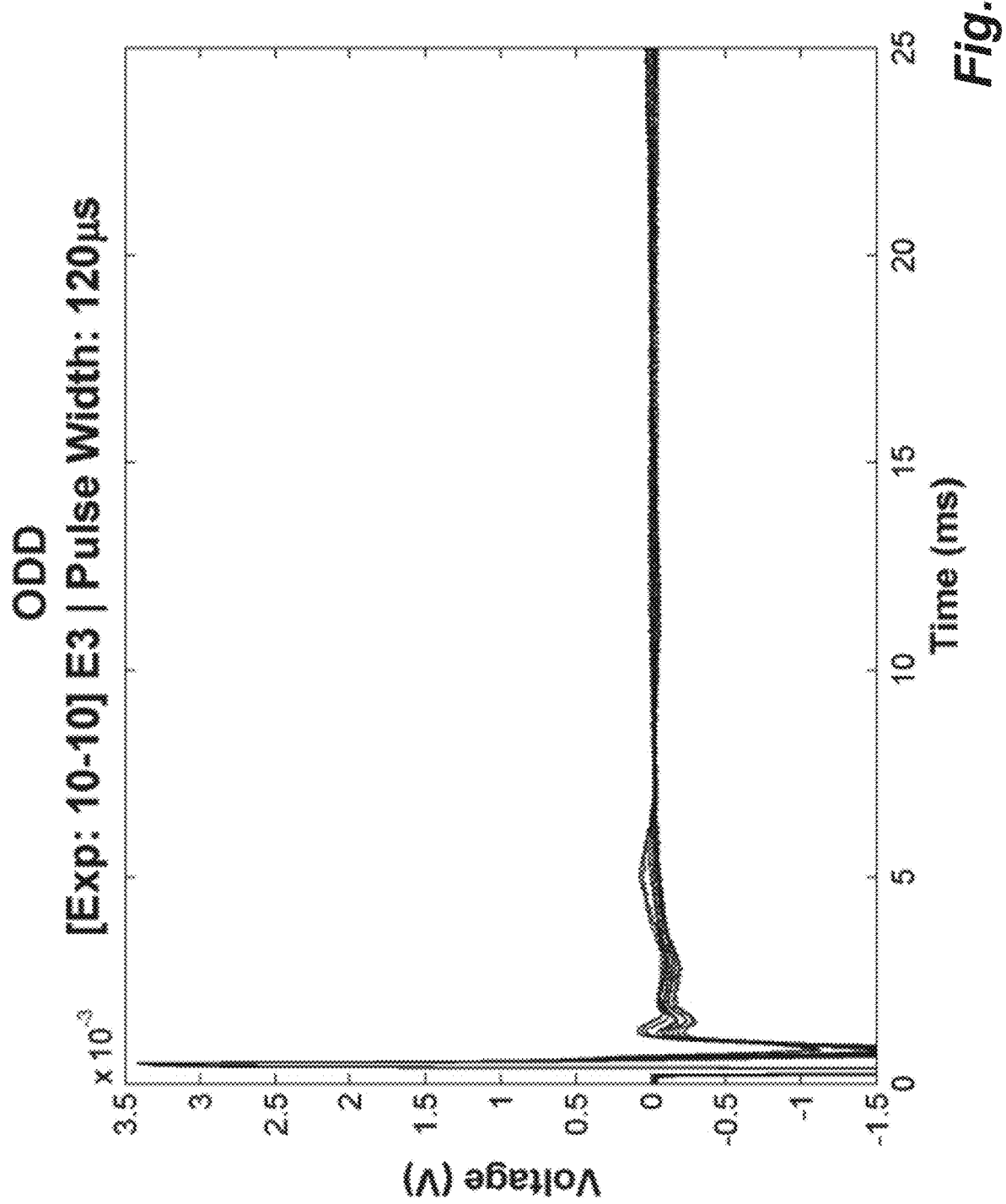

FIG. 13A and FIG. 13B illustrate the effect of administration of anaesthetic to the spinal cord, with a neural response being present prior to administration and largely being absent subsequent to administration. As can be seen, there is a direct correlation between the measured evoked response and the dosage of the anaesthetic. A "partial block" may be effected by ceasing administration of the anaesthetic once the neural response amplitude reduces to a desired level. The technology described herein is suitable for full implantation within the body of a subject and as a result the evoked potential monitoring could be used in the administration of an active compound to produce a therapeutic benefit. The system could be integrated within an implantable pump to control the administration of the compound.

Figure 14A:
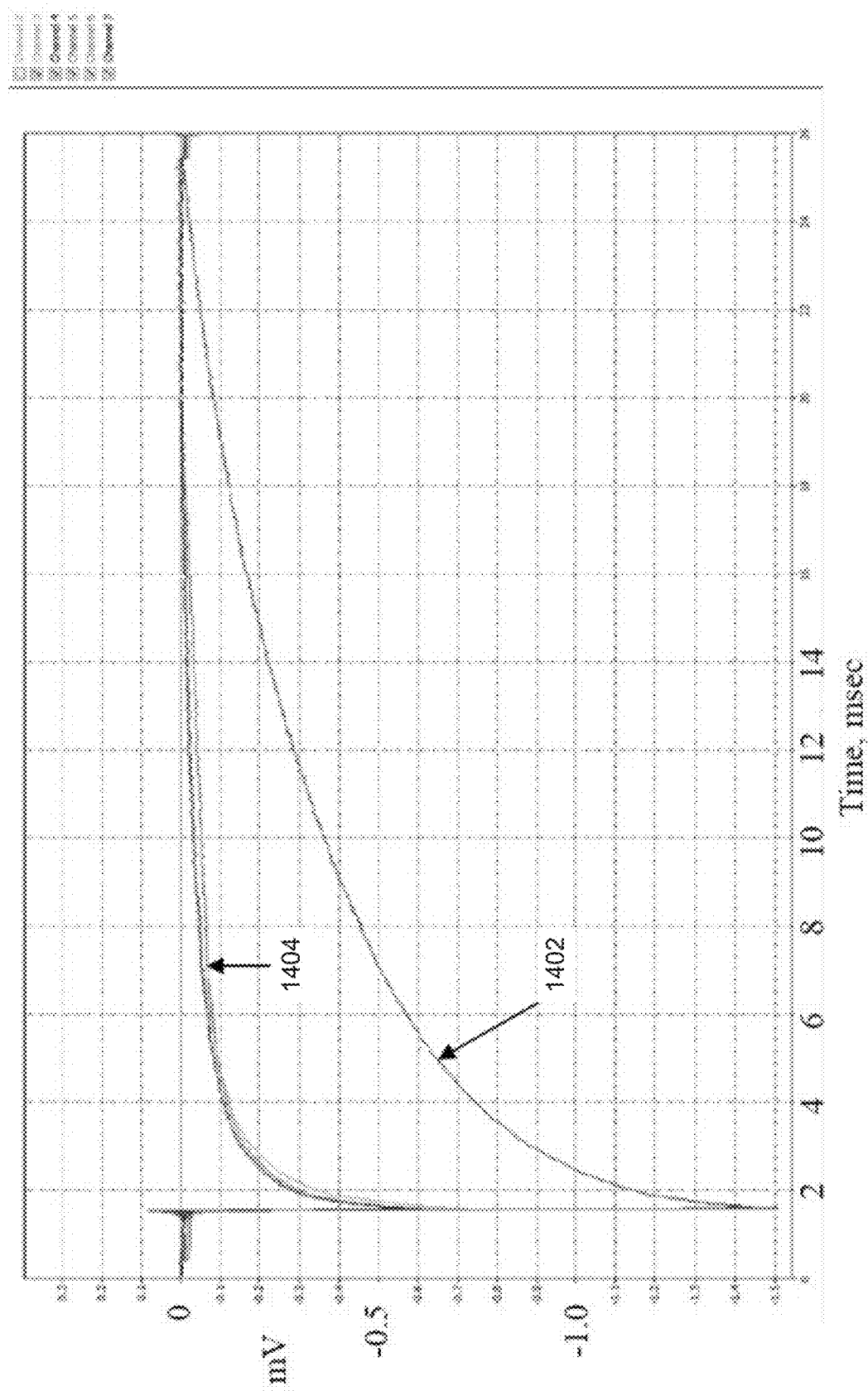
FIG. 14A is a plot showing the artefact arising when electrode shorting is performed.
Figure 14B:
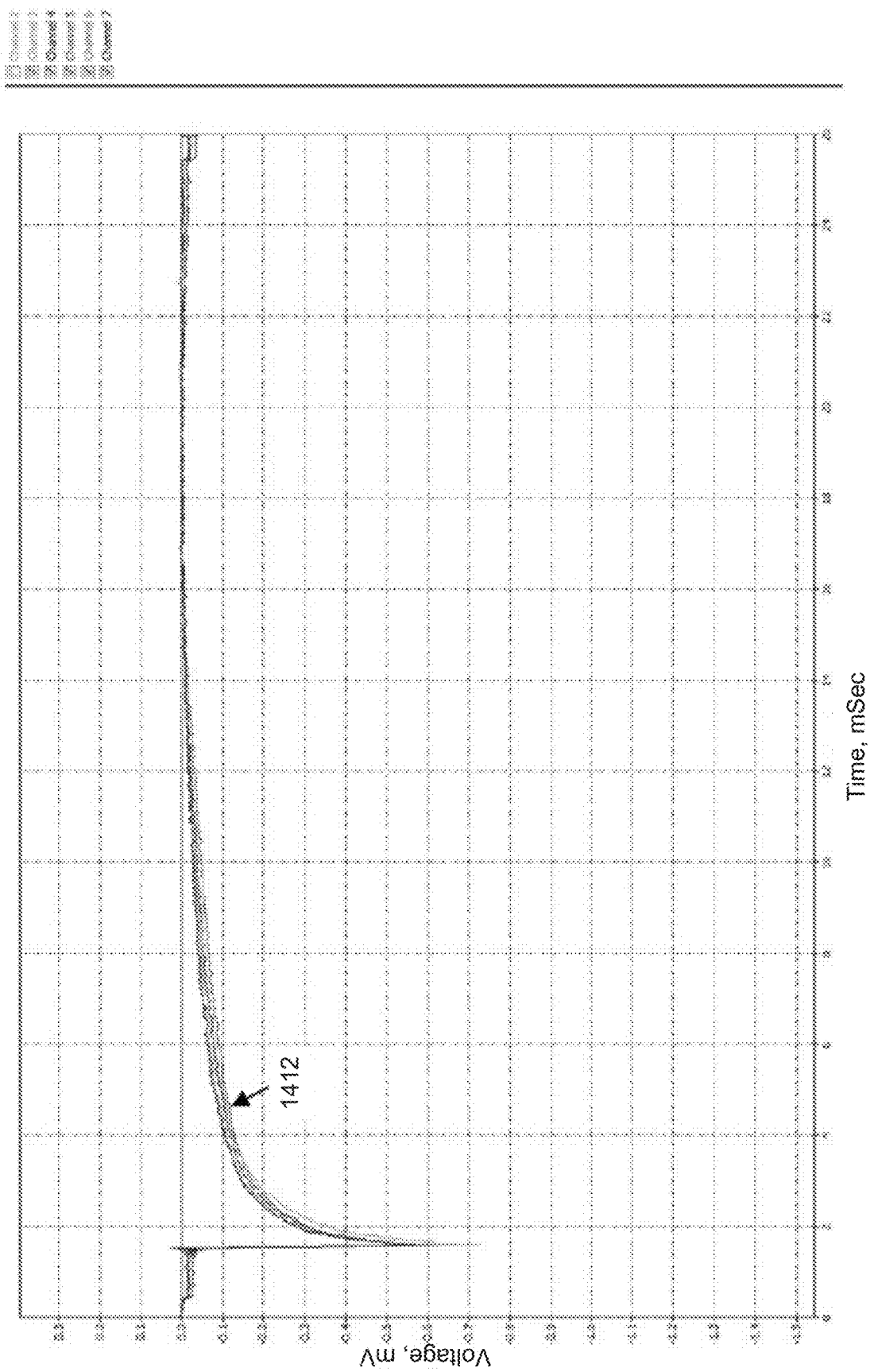
FIG. 14B is a plot showing the artefact arising when the sense electrode is disconnected from the measurement circuitry and from the stimulus electrodes after the stimulus.

FIG. 14A and FIG. 14B shows two plots which compare the artefact arising when electrode shorting is performed, to the artefact arising when the sense electrode is disconnected from the measurement circuitry and from the stimulus electrodes after the stimulus.

The plots of FIG. 14 were obtained from an array placed in a saline bath, and were taken under the following conditions. A stimulation comprising a biphasic pulse of amplitude 10 mA and duration 400 µs was applied using a tripolar configuration, with electrodes E1 and E3 grounded and electrode E2 stimulating, at a stimulus rate of 40 Hz. The artefact measurement of interest (1402, 1412) was obtained on electrode 4 for each plot. Measurements were also obtained on electrodes 5 to 7 using the method of the present invention in both plots, these measurements indicated collectively at 1404, 1412. The measurement parameters for each plot included recovering charge on the stimulus electrodes by short circuiting the stimulus electrodes to each other for 100 µs before stimulation. As shown in FIG. 14A, when the sense electrodes were shorted as taught by prior art methods, the artefact in the measurement 1402 was considerably larger than the artefact present in measurements 1404. In contrast, when the sense electrode E4 was disconnected from the measurement circuitry and from the stimulus electrodes after the stimulus, as taught by the present invention, the artefact in the measurement 1412 from electrode E4 was considerably reduced. The effect of this benefit in preferred embodiments is that an evoked response can be recorded in a single measurement with sufficient signal to noise ratio to permit analysis of the individual evoked response measurement. Moreover, such "single shot" measurements can in some embodiments be obtained in response to normal therapeutic stimuli. This avoids wasting battery power to deliver a train of high power stimuli having parameters which are well outside normal therapeutic settings and thus not of therapeutic benefit, to enable an averaged response to be extracted over a large number of measurements, as is required in systems having poor artefact performance.

It will be appreciated by persons skilled in the art that numerous variations and/or modifications may be made to the invention as shown in the specific embodiments without departing from the spirit or scope of the invention as broadly described. For example in the measurements stages of charge recovery (FIG. 2B), stimulate (FIG. 2C) and delay (FIG. 2D), the sense electrodes are described as being disconnected from the sense circuitry. In the embodiment of FIG. 2 this is effected by setting the sample and hold 208 to "hold", and it is noted that in alternative embodiments the sample and hold 208 may be positioned elsewhere in the measurement chain. Such embodiments are all to be understood to be within the scope of the phrase "disconnecting the sense electrode from the measurement circuitry" or similar as used herein. The present embodiments are, therefore, to be considered in all respects as illustrative and not restrictive.

The invention claimed is:

1. A method for measuring a neural response to an electrical stimulus, the method comprising:
applying the electrical stimulus from stimulus electrodes to neural tissue, while keeping a sense electrode disconnected from measurement circuitry;
imposing, after applying the electrical stimulus, a post-stimulus delay during which the sense electrode is kept disconnected from the measurement circuitry; and
amplifying, after the post-stimulus delay, a neural response signal present at the sense electrode by connecting the sense electrode to the measurement circuitry.

2. The method of claim 1, wherein the sense electrode is open circuited during the post-stimulus delay so as to be disconnected from the stimulus electrodes, to prevent charge transfer to the sense electrode from the stimulus electrodes.

3. The method of claim 1, wherein the stimulus electrodes are open circuited during the post-stimulus delay.

4. The method of claim 1, further comprising settling the measurement circuitry prior to applying the electrical stimulus, by connecting the sense electrode to the measurement circuitry to allow the measurement circuitry to settle towards a bio-electrically defined steady state.

5. The method of claim 4, wherein the settling, applying, imposing and amplifying comprises a measurement cycle, and wherein repeated measurement cycles are undertaken, and wherein the measurement circuitry is allowed to accumulate the bio-electrically defined steady state over the repeated measurement cycles without re-setting the bio-electrically defined steady state each measurement cycle.

6. The method of claim 4, wherein a period of the settling is sufficiently long to permit the sense electrode and the measurement circuitry to reach an equilibrium.

7. The method of claim 1, further comprising recovering charge on the stimulus electrodes prior to applying the electrical stimulus, by short circuiting the stimulus electrodes to each other.

8. The method of claim 1, wherein the post-stimulus delay is in a range of zero to 1 ms.

9. The method of claim 8, wherein the post-stimulus delay is in a range of 50 to 200 μs.

10. The method of claim 1, wherein the post-stimulus delay is set to a value which ensures the measurement circuitry is not saturated and therefore performs linearly at all times without experiencing clipping.

11. The method of claim 1, wherein a feedback loop is implemented to determine a suitable minimum post-stimulus delay which avoids saturation from the electrical stimulus.

12. The method of claim 4, wherein during the settling, the sense electrode is connected to a sample-and-hold circuit at an input of the measurement circuitry.

13. The method of claim 4, wherein a buffer or follower amplifier is provided between the sense electrode and the measurement circuitry.

14. The method of claim 13 wherein the buffer amplifier is configured to give current gain to drive a storage capacitor of a sample and hold circuit.

15. The method of claim 13 wherein a series capacitor is interposed between the sense electrode and the buffer amplifier to avoid DC transfer with the neural tissue.

16. The method of claim 1, wherein the stimulus electrodes and the sense electrode electrodes are selected from an implanted electrode array.

17. The method of claim 1, wherein the amplifying comprises passing the neural response signal from the sense electrode to a single-ended amplifier.

18. The method of claim 1, wherein the amplifying comprises passing the neural response signal from the sense electrode and a second neural response signal from a second sense electrode to a differential amplifier.

19. The method of claim 7 wherein, while recovering charge, the sense electrode is disconnected from the measurement circuitry.

20. The method of claim 1 wherein the sense electrode is within 3 cm of at least one of the stimulus electrodes.

21. The method of claim 1, further comprising using a measurement of the neural response to control the delivery of subsequent electrical stimuli.

22. An implantable device for measuring a neural response to an electrical stimulus, the device comprising:
a plurality of electrodes including a plurality of stimulus electrodes and one or more sense electrodes;
a stimulus source configured to provide the electrical stimulus to be delivered from the plurality of stimulus electrodes to neural tissue;
measurement circuitry configured to amplify a neural response signal sensed at the one or more sense electrodes; and
a control unit configured to control application of the electrical stimulus to the neural tissue and measurement of the neural response, the control unit configured to:
cause the stimulus source to apply the electrical stimulus from the plurality of stimulus electrodes to the neural tissue while keeping the one or more sense electrodes disconnected from the measurement circuitry;
impose, after applying the electrical stimulus, a post-stimulus delay during which the one or more sense electrodes are disconnected from the measurement circuitry; and
amplify, after the post-stimulus delay, the neural response signal present at the one or more sense electrodes by connecting the one or more sense electrodes to the measurement circuitry.

23. The device of claim 22, wherein the plurality of stimulus electrodes are open circuited during the post-stimulus delay.

24. The device of claim 22, wherein the control unit is further configured to:
settle the measurement circuitry prior to the electrical stimulus by connecting the one or more sense electrodes to the measurement circuitry to allow the measurement circuitry to settle towards a bio-electrically defined steady state.

25. The device of claim 22, wherein the control unit is further configured to:
recover charge on the plurality of stimulus electrodes by short circuiting each stimulus electrode of the plurality of stimulus electrodes to each other stimulus electrode of the plurality of stimulus electrodes.

26. The device of claim 22, wherein the control unit is further configured to open circuit the one or more sense electrodes during the post-stimulus delay so as to disconnect the one or more sense electrodes from all other electrodes of the plurality of electrodes, to prevent charge transfer to the one or more sense electrodes from the other electrodes of the plurality of electrodes.

* * * * *